United States Patent [19]

Imae et al.

[11] Patent Number: 4,500,526
[45] Date of Patent: Feb. 19, 1985

[54] CEPHALOSPORIN DERIVATIVES

[75] Inventors: Kiyoto Imae, Ichikawa; Shimpei Aburaki, Tokyo; Yukio Narita; Jun Okumura, both of Yokohama; Takayuki Naito, Kawasaki, all of Japan

[73] Assignee: Bristol-Myers Company, New York, N.Y.

[21] Appl. No.: 541,593

[22] Filed: Oct. 13, 1983

Related U.S. Application Data

[63] Continuation-in-part of Ser. No. 392,866, Jun. 28, 1982, abandoned.

[51] Int. Cl.³ .................. C07D 501/36; A61K 31/545
[52] U.S. Cl. ......................................... 514/226; 544/26; 544/27
[58] Field of Search .................. 544/27, 26, 21, 22; 424/246

[56] References Cited

U.S. PATENT DOCUMENTS

| | | | |
|---|---|---|---|
| 4,278,671 | 7/1981 | Odriai et al. | 424/246 |
| 4,278,793 | 7/1981 | Durckheimer et al. | 544/27 |
| 4,399,131 | 8/1983 | Durckheimer et al. | 544/22 |

FOREIGN PATENT DOCUMENTS 1399086  6/1977  United Kingdom .

Primary Examiner—Nicholas S. Rizzo
Attorney, Agent, or Firm—Richard R. Lloyd

[57] ABSTRACT

Compounds of the formula

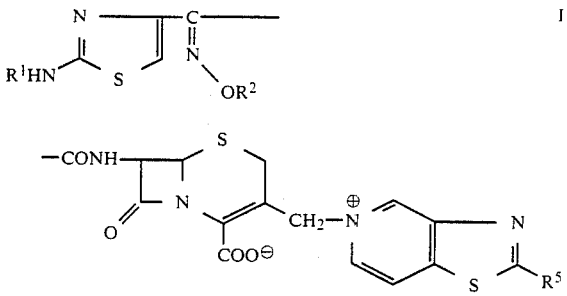

wherein $R^1$ is hydrogen or a conventional amino-protecting group, $R^2$ is one of various alkyl, alkenyl, alkynyl, cycloalkyl, carboxyalkyl or carboxycycloalkyl moieties described herein, and $R^5$ is hydrogen, amino, carboxy, formyl, carbamoyl, guanidino, amidino or one of various alkyl, alkoxy, alkylthio or substituted amino moieties described herein, and nontoxic pharmaceutically acceptable acid addition salts, physiologically hydrolyzable esters and solvates thereof, as well as processes for their preparation, are disclosed. The compounds in which $R^1$ is hydrogen are potent antibacterial agents.

23 Claims, No Drawings

CEPHALOSPORIN DERIVATIVES

CROSS-REFERENCE TO RELATED APPLICATION

This application is a continuation-in-part of our prior, co-pending application Ser. No. 392,866, filed June 28, 1982, now abandoned.

SUMMARY OF THE INVENTION

This invention relates to novel cephalosporin derivatives of the formula

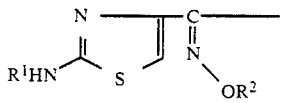

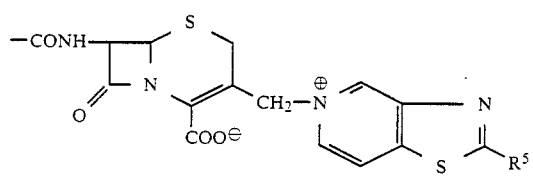

wherein $R^1$ is hydrogen or a conventional amino-protecting group, $R^2$ is a straight or branched chain alkyl group containing from 1 to 4 carbon atoms, allyl, propargyl, 2-butenyl, 2-butynyl, 3-butenyl, 3-butynyl, cyclo(lower)alkyl or a group of the formula

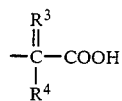

in which $R^3$ and $R^4$ each are independently hydrogen, methyl or ethyl, or $R^3$ and $R^4$, taken together with the carbon atom to which they are attached, may be a cycloalkylidene ring containing from 3 to 5 carbon atoms, and $R^5$ is hydrogen, carboxy, formyl, amino, carbamoyl, (lower)alkylamino, di(lower)alkylamino, guanidino, amidino, (lower)alkyl, (lower)alkoxy, (lower)alkylthio or a group of the formula

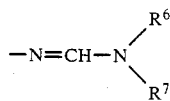

in which $R^6$ and $R^7$ each are independently hydrogen or (lower)alkyl, or when taken together with the nitrogen atom to which they are attached, $R^6$ and $R^7$ represent a 5 to 7-membered saturated ring optionally containing an additional hetero atom selected from N, O and S, or $R^5$ is a group of the formula

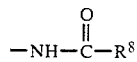

in which $R^8$ is hydrogen, (lower)alkyl, amino(lower)alkyl, (lower)alkoxy, amino, (lower)alkylamino or

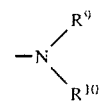

in which $R^9$ and $R^{10}$ are each (lower)alkyl or, when taken together with the nitrogen atom to which they are attached, $R^9$ and $R^{10}$ represent a 5 to 7-membered saturated ring optionally containing an additional hetero atom selected from N, O and S, and nontoxic pharmaceutically acceptable salts, physiologically hydrolyzable esters of solvates thereof. Processes for their preparation also are described.

DESCRIPTION OF THE PRIOR ART

U.K. Patent Specification No. 1,399,086 contains a generic disclosure encompassing a vast number of cephalosporins of the formula

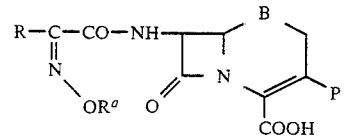

wherein R is hydrogen or an organic group, $R^a$ is an etherifying monovalent organic group linked to the oxygen through a carbon atom, B is $>S$ or $>S\rightarrow O$, and P is an organic group. However, the 2-aminothiazol-4-yl group is not identified as a possible R substituent. Although P may be the group —CH$_2$Y in which Y may be the residue of a nitrogen-containing heterocycle, only pyridinium and 4-carbamoylpyridinium are exemplified, and there is no suggestion that Y may be the 5-thiazolo[4,5-c]pyridinio moiety. U.S. Pat. No. 3,971,778 and its divisionals U.S. Pat. Nos. 4,024,133, 4,024,137, 4,064,346, 4,033,950, 4,079,178, 4,091,209, 4,092,477 and 4,093,803 have similar disclosures.

U.S. Pat. No. 4,278,793 contains a generic disclosure encompassing a vast number of cephalosporin derivatives of the formula

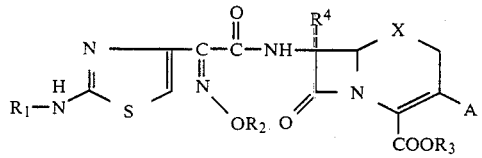

in which the variables $R_1$, $R_2$, $R_3$, $R_4$, X and A include generic definitions of the corresponding substituents of the compounds of Formula I claimed herein. Substituent A may be the group —CH$_2$Y in which Y may be the residue of a nucleophilic group (the only heterocyclic rings disclosed for Y are pyridinium, quinolinium and isoquinolinium). In the 20 columns of definitions of the various substituent groups, the 78 page long table of structural formulae and the 225 examples, there is no disclosure that A may be the 5-thiazolo[4,5-c]pyridinio moiety. United Kingdom Patent Specification No. 1,604,971 is concordant thereto and has a substantially identical disclosure. Published United Kingdom Patent Application No. 2,028,305 A, although apparently not formally related, contains the same broad generic disclosure but exemplifies A only as hydrogen.

U.S. Pat. No. 4,278,671 discloses 7-[2-(2-aminothiazol-4-yl)-2-(syn)-methoxyiminoacetamido]cephalosporin derivatives of the formula

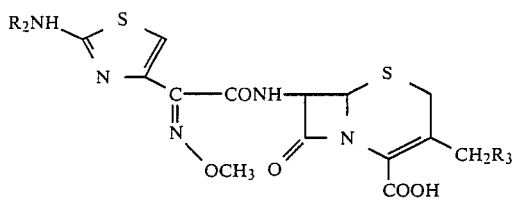

in which R₂NH is an optionally protected amino group and R₃ is hydrogen or "the residue of a nucleophilic compound". The term "the residue of a nucleophilic compound" is broadly defined and it is then stated that R³ "may alternatively be a quaternary ammonium group". Only pyridinium, variously substituted pyridinium, quinolinium, picolinium and lutidinium are disclosed as possible quaternary ammonium groups. There is no suggestion that the quaternary ammonium group may be the 5-thiazolo[4,5-c]pyridinio moiety. United Kingdom Patent Specification No. 1,581,854 is concordant thereto and has a substantially identical disclosure. Other patents to the same patentee, which are not formally related but which have similar disclosures, include U.S. Pat. No. 4,098,888 and its divisionals U.S. Pat. Nos. 4,203,899, 4,205,180, 4,298,606 and United Kingdom Patent Specification No. 1,536,281.

COMPLETE DISCLOSURE

This invention relates to novel cephalosporin derivatives of the formula

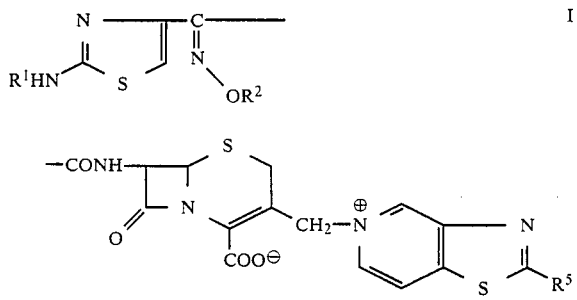

I wherein $R^1$ is hydrogen or a conventional amino-protecting group, $R^2$ is a straight or branched chain alkyl group containing from 1 to 4 carbon atoms, allyl, propargyl, 2-butenyl, 2-butynyl, 3-butenyl, 3-butynyl, cyclo(lower)alkyl or a group of the formula

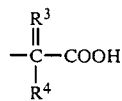

in which $R^3$ and $R^4$ each are independently hydrogen, methyl or ethyl, or $R^3$ and $R^4$, taken together with the carbon atom to which they are attached, may be a cycloalkylidene ring containing from 3 to 5 carbon atoms, and $R^5$ is hydrogen, carboxy, formyl, amino, carbamoyl, (lower)alkylamino, di(lower)alkylamino, guanidino, amidino, (lower)alkyl, (lower)alkoxy, (lower)alkylthio or a group of the formula

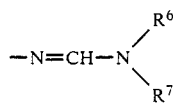

in which $R^6$ and $R^7$ each are independently hydrogen or (lower)alkyl, or when taken together with the nitrogen atom to which they are attached, $R^6$ and $R^7$ represent a 5 to 7-membered saturated ring optionally containing an additional hetero atom selected from N, O and S, or $R^5$ is a group of the formula

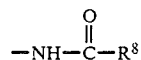

in which $R^8$ is hydrogen, (lower)alkyl, amino(lower)alkyl, (lower)alkoxy, amino, (lower)alkylamino or

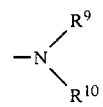

in which $R^9$ and $R^{10}$ are each (lower)alkyl or, when taken together with the nitrogen atom to which they are attached, $R^9$ and $R^{10}$ represent a 5 to 7-membered saturated ring optionally containing an additional hetero atom selected from N, O and S, and nontoxic pharmaceutically acceptable salts and physiologically hydrolyzable esters thereof, as well as processes for their preparation. Also included within the scope of this invention are the solvates (including hydrates) of the compounds of Formula I, as well as the tautomeric forms of the compounds of Formula I, e.g. the 2-iminothiazolin-4-yl form of the 2-aminothiazol-4-yl moiety.

As shown in the structural formula, the compounds of Formula I have the "syn" or "Z" configuration with respect to the alkoxyimino group. Because the compounds are geometric isomers, some of the "anti" isomer may also be present. This invention comprises compounds of Formula I containing at least 90% of the "syn" isomer. Preferably the compounds of Formula I are "syn" isomers which are essentially free of the corresponding "anti" isomers.

The nontoxic pharmaceutically acceptable acid addition salts of the compounds of Formula I include, for example, the salts with hydrochloric, hydrobromic, formic, nitric, sulfuric, methanesulfonic, phosphoric, acetic and trifluoroacetic acids, and other acids which have been used in the penicillin and cephalosporin art.

The compounds of Formula I in which $R^1$ is hydrogen exhibit high antibacterial activity against various Gram positive and Gram negative bacteria, and are useful in the treatment of bacterial infections in animals, including man. The compounds of Formula I may be formulated for parenteral use in a conventional manner utilizing known pharmaceutical carriers and excipients, and may be presented in unit dosage form or in multidosage containers. The compositions may be in the form of solutions, suspensions or emulsions in oily or aqueous vehicles, and may contain conventional dispersing, suspending or stabilizing agents. The compositions may also be in the form of a dry powder for reconstitution before use, e.g. with sterile, pyrogen-free water. The compounds of Formula I may also be formulated as suppositories utilizing conventional suppository bases such as cocoa butter or other glycerides. The compounds of this invention may, if desired, be administered in combination with other antibiotics such as penicillins or other cephalosporins.

When provided in unit dosage forms the compositions will preferably contain from about 50 to about 1500 mg of the active ingredient of Formula I. The dosage of the compounds of Formula I is dependent on such factors as the weight and age of the patient as well as the particular nature and severity of the disease, and is within the discretion of the physician. However, the dosage for adult human treatment will usually be in the range of from about 500 to about 5000 mg per day, depending on the frequency and route of administration. When administered intramuscularly or intravenously to an adult human, a total dosage of from about 750 to about 3000 mg per day, in divided doses, normally will be sufficient, although higher daily doses of some of the compounds may be desirable in the case of Pseudomonas infections.

The preferred compounds of Formula I are those in which $R^1$ is hydrogen and $R^2$ is methyl, ethyl, allyl, propargyl, carboxymethyl or a group of the formula

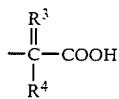

in which $R^3$ and $R^4$ each are methyl, or $R^3$ and $R^4$, taken together with the carbon atom to which they are attached, are cyclopropylidene or cyclobutylidene. Particularly preferred compounds are those in which $R^1$ is hydrogen, $R^2$ is methyl, ethyl, 2-carboxyprop-2-yl, propargyl, carboxymethyl or 1-carboxycyclobut-1-yl, and $R^5$ is hydrogen, methyl, formyl, carbo(lower)alkoxyamino, (lower)alkanoylamino, glycylamino, di(lower)alkylamino, formylamino, carbamoyl or amino. The most preferred compounds of the invention are
(1) 7-[(Z)-2-(2-aminothiazol-4-yl)-2-methoxyiminoacetamido]-3-{(5-thiazolo[4,5-c]pyridinio)methyl}-3-cephem-4-carboxylate,
(2) 7-[(Z)-2-(2-aminothiazol-4-yl)-2-(2-carboxyprop-2-oxyimino)-acetamido]-3-{(5-thiazolo[4,5-c]pyridinio)methyl}-3-cephem-4-carboxylate,
(3) 7-[(Z)-2-(2-aminothiazol-4-yl)-2-ethoxyiminoacetamido]-3-{(5-thiazolo[4,5-c]pyridinio)methyl}-3-cephem-4-carboxylate,
(4) 7-[(Z)-2-(2-aminothiazol-4-yl)-2-(1-carboxycyclobut-1-oxyimino)acetamido]-3-{(5-thiazolo[4,5-c]pyridinio)methyl}-3-cephem-4-carboxylate,
(5) 7-[(Z)-2-(2-aminothiazol-4-yl)-2-methoxyiminoacetamido]-3-[{5-(2-aminothiazolo[4,5-c]pyridinio)}methyl]-3-cephem-4-carboxylate,
(6) 7-[(Z)-2-(2-aminothiazol-4-yl)-2-methoxyiminoacetamido]-3-[{5-(2-methylthiazolo[4,5-c]pyridinio)}methyl]-3-cephem-4-carboxylate,
(7) 7-[(Z)-2-(2-aminothiazol-4-yl)-2-(propargyloxyimino)-acetamido]-3-(2-amino-5-thiazolo[4,5-c]pyridinio)methyl-3-cephem-4-carboxylate,
(8) 7-[(Z)-2-(2-aminothiazol-4-yl)-2-(carboxymethoxyimino)-acetamido]-3-(2-amino-5-thiazolo[4,5-c]pyridinio)methyl-3-cephem-4-carboxylate,
(9) 7-[(Z)-2-(2-aminothiazol-4-yl)-2-(1-carboxycyclobut-1-oxyimino)acetamido]-3-(2-amino-5-thiazolo[4,5-c]pyridinio)-methyl-3-cephem-4-carboxylate,
(10) 7-[(Z)-2-(2-aminothiazol-4-yl)-2-(1-carboxycyclobut-1-oxyimino)acetamido]-3-(2-methyl-5-thiazolo[4,5-c]pyridinio)-methyl-3-cephem-4-carboxylate,
(11) 7-[(Z)-2-(2-aminothiazol-4-yl)-2-allyloxyiminoacetamido]-3-[{5-(thiazolo[4,5-c]pyridinio)}methyl]-3-cephem-4-carboxylate,
(12) 7-[(Z)-2-(2-aminothiazol-4-yl)-2-(2-carboxyprop-2-oxyimino)-acetamido]-3-[{5-(2-aminothiazolo[4,5-c]pyridinio)methyl]-3-cephem-4-carboxylate,
(13) 7-[(Z)-2-(2-aminothiazol-4-yl)-2-methoxyiminoacetamido]-3-(2-acetylamino-5-thiazolo[4,5-c]pyridinio)methyl-3-cephem-4-carboxylate,
(14) 7-[(Z)-2-(2-aminothiazol-4-yl)-2-methoxyiminoacetamido]-3-(2-glycylamino-5-thiazolo[4,5-c]pyridinio)methyl-3-cephem-4-carboxylate,
(15) 7-[(Z)-2-(2-aminothiazol-4-yl)-2-methoxyiminoacetamido]-3-(2-dimethylamino-5-thiazolo[4,5-c]pyridinio)methyl-3-cephem-4-carboxylate,
(16) 7-[(Z)-2-(2-aminothiazol-4-yl)-2-methoxyiminoacetamido]-3-(2-formyl-5-thiazolo[4,5-c]pyridinio)methyl-3-cephem-4-carboxylate and
(17) 7-[(Z)-2-(2-aminothiazol-4-yl)-2-methoxyiminoacetamido]-3-(2-carbamoyl-5-thiazolo[4,5-c]pyridinio)methyl-3-cephem-4-carboxylate.

In the primary evaluation of the compounds of this invention, the Minimum Inhibitory Concentrations (MIC's) of the compounds were determined by the two-fold serial agar dilution method in Mueller-Hinton agar against 32 strains of test organisms in six groups. The sample weights of the test compounds were adjusted according to the purity of each compound, so as to give a more accurate measure of the MIC's. The geometric means of the MIC's determined in these tests are shown in Table 1.

TABLE 1

| Compound of Example | Estimated Purity (%) | Geometric Mean of MIC (mcg/ml) | | | | | |
|---|---|---|---|---|---|---|---|
| | | (G+)-Ia (5 strains) | (G+)-Ib (5) | (G−)-Ia (5) | (G−)-Ib (6) | (G−)-II (5) | (G−)-III (6) |
| 1 = (Ia) | 80 | 0.42 | 0.96 | 0.020 | 0.16 | 0.16 | 2.6 |
| 3 = (Ib) | 80 | 0.42 | 0.96 | 0.035 | 0.22 | 0.32 | 2.6 |
| 4 = (Ic) | 70 | 0.32 | 0.56 | 0.053 | 0.44 | 0.66 | 3.9 |
| 5 = (Id) | 80 | 4.4 | 8.8 | 0.040 | 0.71 | 0.88 | 1.4 |
| 7 = (Ie) | 70 | 2.2 | 4.4 | 0.023 | 0.50 | 0.34 | 1.3 |
| 8 = (If) | 45 | 0.3 | 0.8 | 0.029 | 0.40 | 0.35 | 2.1 |
| 9 = (Ig) | 75 | 2.1 | 3.6 | 0.0072 | 0.30 | 0.10 | 1.8 |
| 10 = (Ih) | 65 | 0.34 | 0.78 | 0.0070 | 0.058 | 0.11 | 2.3 |
| 11 = (Ii) | 50 | 0.23 | 0.20 | 0.025 | 0.13 | 0.24 | 5.5 |
| 12 = (Ij) | 30 | 0.36 | 0.48 | 0.020 | 0.17 | 0.24 | 3.0 |
| 13 = (Ik) | 80 | 1.4 | 3.3 | 0.015 | 0.36 | 0.27 | 1.4 |

TABLE 1-continued

| Compound of Example | Estimated Purity (%) | Geometric Mean of MIC (mcg/ml) | | | | | |
|---|---|---|---|---|---|---|---|
| | | (G+)-Ia (5 strains) | (G+)-Ib (5) | (G−)-Ia (5) | (G−)-Ib (6) | (G−)-II (5) | (G−)-III (6) |
| 14 = (Im) | 70 | 3.4 | 8.8 | 0.027 | 0.56 | 0.25 | 2.5 |
| 15 = (In) | 60 | 0.32 | 0.72 | 0.010 | 0.096 | 0.17 | 1.9 |
| 16 = (Io) | 60 | 1.6 | 3.8 | 0.023 | 0.47 | 0.66 | 1.5 |
| 17 = (Ip) | 80 | 0.34 | 0.80 | 0.037 | 0.40 | 0.68 | 11 |
| 18 = (Iq) | 60 | 0.92 | 2.4 | 0.038 | 0.61 | 0.69 | 10 |
| 19 = (Ir) | 40 | 0.40 | 0.80 | 0.025 | 0.46 | 0.52 | 5.2 |
| 20 = (Is) | 40 | 0.46 | 0.80 | 0.038 | 0.69 | 0.60 | 14 |
| 21 = (It) | 65 | 0.53 | 1.6 | 0.30 | 0.92 | 2.8 | 34 |
| 22 = (Iu) | 65 | 0.46 | 0.80 | 0.012 | 0.11 | 0.23 | 6.3 |
| 23 = (Iv) | 85 | 1.6 | 3.1 | 0.014 | 1.2 | 0.69 | 5.7 |
| 24 = (Iw) | 55 | 0.53 | 1.6 | 0.016 | 0.17 | 0.20 | 1.7 |
| 25 = (Ix) | 65 | 0.53 | 0.80 | 0.022 | 0.20 | 0.39 | 2.8 |

(G+)-Ia: Penicillin-sensitive *S. aureus* (5 strains)
(G+)-Ib: Penicillin-resistant *S. aureus* (5 strains)
(G−)-Ia: Cephalothin-sensitive *E. coli* (2 strains), *Kl. pneumoniae* (1 strain) and *Pr. mirabilis* (2 strains)
(G−)-Ib: Cephalothin-resistant *E. coli* (3 strains) and *Kl. pneumoniae* (3 strains)
(G−)-II: *M. morganii* (1 strain), *Ent. cloacae* (2 strains) and *Ser. marcescens* (2 strains)
(G−)-III: *Ps. aeruginosa* (6 strains)

The absorption of some of the preferred compounds were determined in mice following a single intramuscular injection of the test compound (dissolved in 0.1M phosphate buffer; pH 7) at a dosage of 20 mg/kg. Blood samples were collected from the orbital sinuses into heparinized capillary tubes and assayed in Nutrient Agar (pH 6.6) using *E. coli* Ess-22-31 as the test organism. The blood levels at various time intervals, the half-life values ($t_{\frac{1}{2}}$) and the areas under the curve (AUC) are shown in Table 2.

TABLE 2

| | Mouse Blood Levels | | | | | | | | | |
|---|---|---|---|---|---|---|---|---|---|---|
| | Mouse Blood Level (mcg/ml) Minutes After Administration | | | | | | | | T ½ (min) | AUC (mcg · hr/ml) |
| Compound | 10 | 20 | 30 | 40 | 50 | 60 | 90 | 120 | | |
| Ia | 20 | 15 | 11 | 8.6 | 6.9 | 6.5 | 3.1 | 2.1 | 35 | 15 |
| Ib | 15 | 22 | 8.4 | 6.1 | 3.8 | 0.92 | 0.68 | 0.43 | 19 | 8.4 |
| Ic | 18 | 14 | 10 | 8.2 | 5.8 | 3.6 | 1.9 | 1.3 | 28 | 12 |
| Id | 16 | 14 | 11 | 6.1 | 3.9 | 2.5 | 0.72 | <0.2 | 16 | 9.5 |
| Ie | 13 | 12 | 7.5 | 4.3 | 3.0 | 2.6 | 0.51 | 0.15 | 16 | 7.9 |
| If | 14 | 11 | 7.3 | 4.2 | 3.6 | 3.3 | 2.0 | 1.2 | 34 | 9.1 |
| Ig | 21 | 17 | 15 | 10 | 7.6 | 6.3 | 1.9 | 0.84 | 22 | 15 |
| Ih | 16 | 10 | 6.9 | 5.9 | 4.1 | 3.0 | 0.79 | 0.13 | 16 | 8.6 |
| Ii | 14 | 10 | 5.9 | 4.8 | 2.4 | 1.5 | 0.25 | <0.1 | 13 | 6.8 |
| Ik | 20 | 16 | 11 | 8.2 | 5.2 | 4.1 | 1.8 | 0.67 | 22 | 13 |
| Im | 13 | 10 | 6.9 | 4.8 | 2.7 | 2.0 | 0.48 | <0.2 | 16 | 7.1 |
| In | 14 | 14 | 7.6 | 7.0 | 4.4 | 3.9 | 2.9 | 1.0 | 29 | 11 |
| Ip | 24 | 18 | 13 | 10 | 6.8 | 5.5 | 2.5 | 1.4 | 27 | 16 |
| Iq | 15 | 17 | 12 | 11 | 9.9 | 8.8 | 3.4 | 1.5 | 28 | 16 |
| Is | 19 | 18 | 14 | 6.7 | 4.6 | 4.6 | 2.2 | 1.1 | 26 | 13 |
| It | 19 | 18 | 11 | 7.8 | 6.6 | 5.4 | 2.1 | 0.89 | 24 | 13 |
| Iu | 18 | 13 | 9.6 | 5.5 | 3.4 | 2.6 | 1.0 | 0.34 | 19 | 9.8 |
| Iv | 17 | 16 | 10 | 5.9 | 4.3 | 3.0 | 1.2 | <0.2 | 19 | 10 |
| Iw | 20 | 19 | 8.9 | 6.6 | 3.9 | 2.0 | 1.0 | 0.48 | 19 | 11 |
| Ix | 20 | 18 | 20 | 13 | 11 | 7.0 | 4.2 | 2.1 | 31 | 19 |

The in vitro activity of some of the preferred compounds against 30 strains of fastidious bacteria was determined by the two-fold serial agar dilution method in Gonococcus agar (GC agar), and the results are shown in Table 3.

TABLE 3

In Vitro Activity of Some Preferred Compounds Against Fastidious Bacteria

| Test Organism | Geometric Mean of MIC (mcg/mL) | | |
|---|---|---|---|
| | Ia | Id | Ie |
| *S. pyogenes* (5 strains) | 0.0125 | 0.20 | 0.20 |
| *S. pneumoniae* (5) | 0.0125 | 0.20 | 0.20 |
| *N. gonorrhoeae* (5) | 0.0125 | 0.10 | 0.10 |
| *N. meningitidis* (5) | 0.0125 | 0.10 | 0.10 |
| *H. influenzae* (7) (ampicillin sensitive) | 0.0125 | 0.10 | 0.10 |
| *H. influenzae* (3) (ampicillin resistant) | 0.0125 | 0.10 | 0.10 |

The median protective dose (PD$_{50}$) of some of the preferred compounds against various microorganisms was determined in mice by intramuscular administration of the test compound immediately after an intraperitoneal bacterial challenge. The results are shown in Table 4.

TABLE 4

| | In Vivo Activity | | | | | |
|---|---|---|---|---|---|---|
| | $PD_{50}$ (mg/kg, im) | | | | | |
| | Microorganism | | | | | |
| Compound | S. aureus Smith | S. aureus BX-1633 | E. coli Juhl | P. aeruginosa A9843 | P. aeruginosa A21509 | S. pyogenes A20201 |
| Ia | 0.45 | 0.75 | 0.012 | 7.2 | 6.25 | — |
| Ic | 1.1 | — | 0.048 | 8.6 | — | — |
| Id | 7.2 | 21 | 0.082 | 4.3 | 5.0 | 0.23 |
| Ie | 3.1 | — | 0.08 | 1.8 | — | — |
| If | 0.36 | — | 0.013 | 3.3 | — | — |
| Ik | 3.0 | — | 0.046 | 5.5 | — | — |
| Im | 9.4 | — | 0.1 | 9.0 | — | — |
| In | 0.9 | — | <0.01 | 2.8 | — | — |
| Ip | 1.0 | — | 0.29 | 16 | — | — |
| Iq | 1.8 | — | 0.015 | 12 | — | — |
| Is | 1.2 | — | 0.018 | 10 | — | — |
| It | 1.9 | — | 0.2 | >25 | — | — |
| Iu | 0.48 | — | 0.013 | 4.6 | — | — |
| Iv | 2.6 | — | 0.024 | 21 | — | — |
| Iw | 1.3 | — | 0.015 | 4.7 | — | — |
| Ix | 1.5 | — | 0.013 | — | — | — |

In another aspect, this invention relates to processes for the preparation of the compounds of Formula I. There are two basic procedures for converting a readily available starting cephalosporin to another cephalosporin having different substituents on the 7- and 3-positions. One may first remove the 7-substituent and replace it with the desired 7-substituent, and then insert the desired 3-substituent. Alternatively, one may first insert the desired 3-substituent and subsequently exchange the 7-substituent. The compounds of Formula I may be prepared by either procedure and both are included within the scope of this invention, but it is preferred to insert the desired 7-substituent first and then insert the desired 3-substituent. The preferred procedure is shown below in Reaction Scheme 1 while the alternative procedure is shown in Reaction Scheme 2. In each reaction scheme, n may be 0 or 1. The abbreviation "Tr" represents the trityl (triphenylmethyl) group, which is a preferred amino-protecting group. The abbreviation "Ph" represents the phenyl group. Thus, the —CH(Ph)$_2$ moiety is the benzhydryl group, which is a preferred carboxyl-protecting group.

Reaction Scheme 1

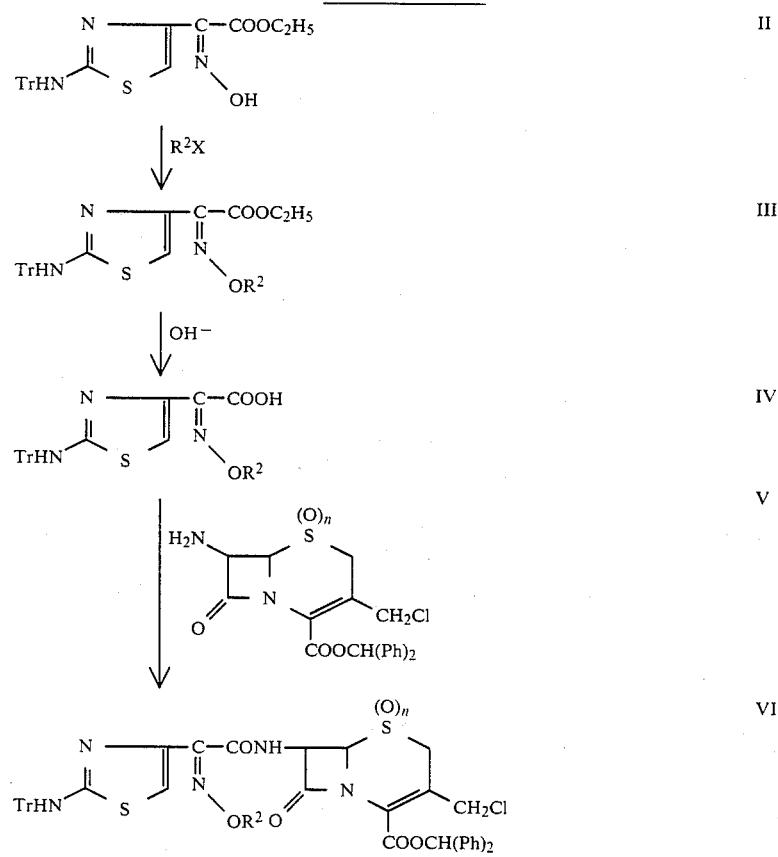

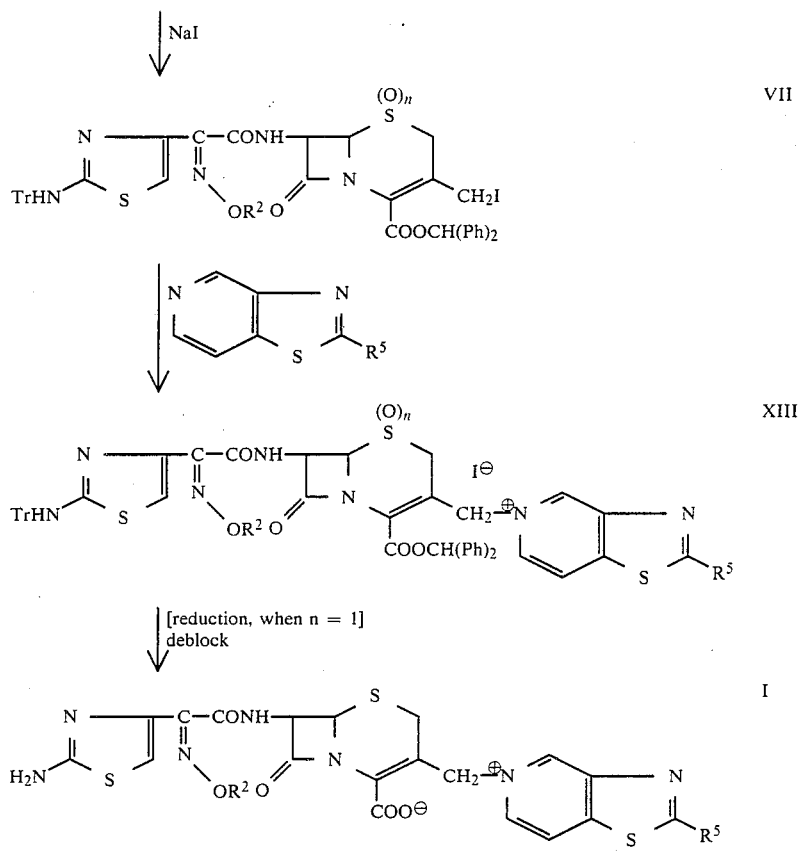
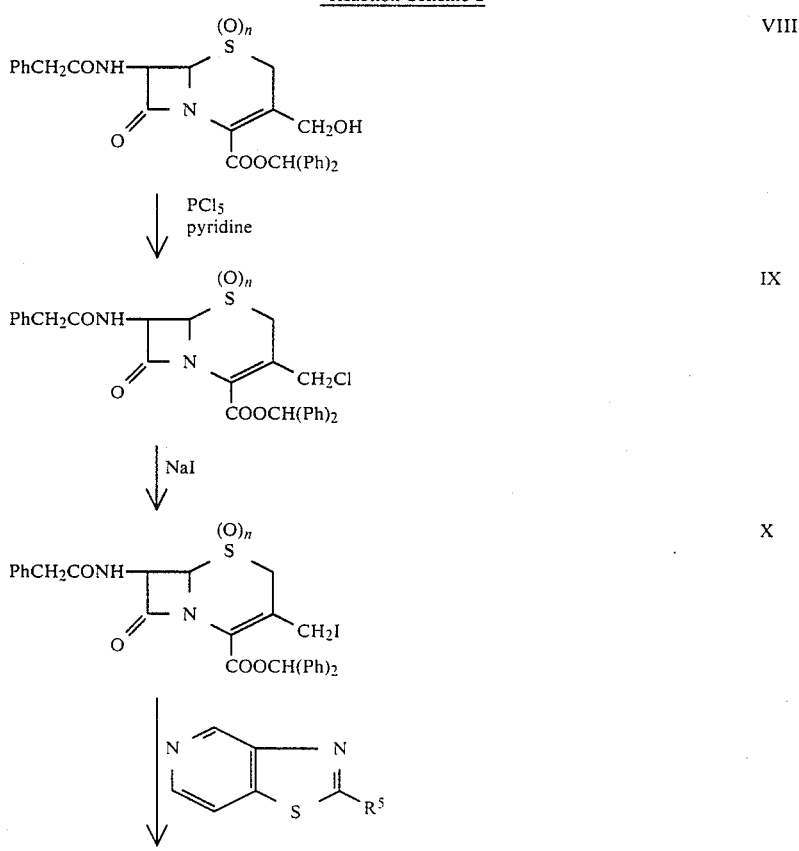
Reaction Scheme 2

-continued

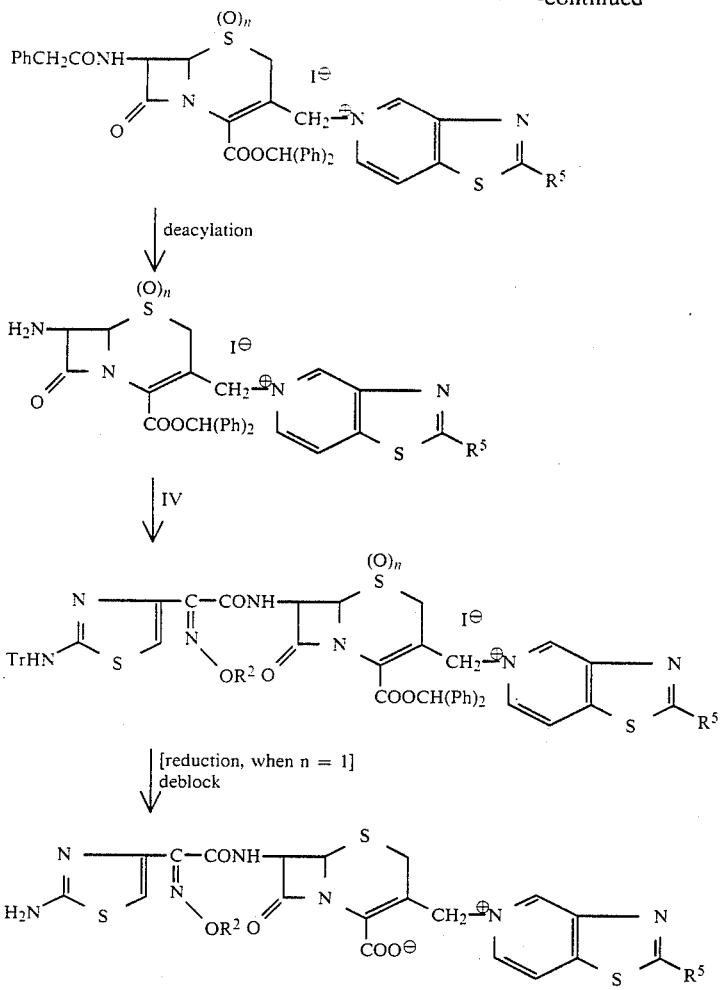

Although the above Reaction Schemes show preferred multi-step procedures for the preparation of the compounds of Formula I, it will be appreciated that other starting materials and procedures may be utilized to prepare the intermediates used in the key step of each Reaction Scheme. Thus, the key step in Reaction Scheme 1 is the reaction of Compound VII with the thiazolo[4,5-c]pyridine. Compound VII may itself be prepared by other procedures. Similarly, the key step in Reaction Scheme 2 is the acylation of Compound XII with Compound IV. Both compounds XII and IV may be prepared by other procedures.

The present invention provides a process for the preparation of compounds of the formula

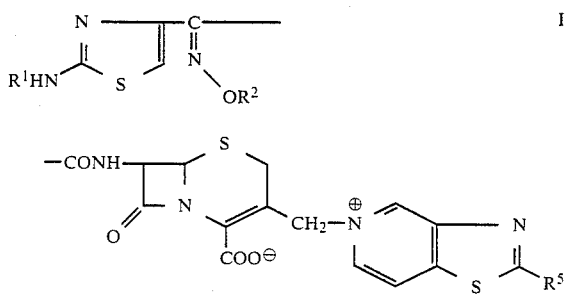

wherein $R^1$ is hydrogen or a conventional amino-protecting group, $R^2$ is a straight or branched chain alkyl group containing from 1 to 4 carbon atoms, allyl, propargyl, 2-butenyl, 2-butynyl, 3-butenyl, 3-butynyl, cyclo(lower)alkyl or a group of the formula

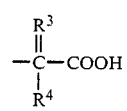

in which $R^3$ and $R^4$ each are independently hydrogen, methyl or ethyl, or $R^3$ and $R^4$, taken together with the carbon atom to which they are attached, may be a cycloalkylidene ring containing from 3 to 5 carbon atoms, and $R^5$ is hydrogen, carboxy, formyl, amino, carbamoyl, (lower)alkylamino, di(lower)alkylamino, guanidino, amidino, (lower)alkyl, (lower)alkoxy, (lower)alkylthio or a group of the formula

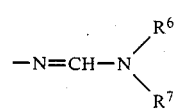

in which $R^6$ and $R^7$ each are independently hydrogen or (lower)alkyl, or when taken together with the nitrogen atom to which they are attached, $R^6$ and $R^7$ represents a 5 to 7-membered saturated ring optionally containing an additional hetero atom selected from N, O and S, or $R^5$ is a group of the formula

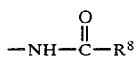

in which $R^8$ is hydrogen, (lower)alkyl, amino(lower)alkyl, (lower)alkoxy, amino, (lower)alkylamino or

in which $R^9$ and $R^{10}$ are each (lower)alkyl or, when taken together with the nitrogen atom to which they are attached, $R^9$ and $R^{10}$ represent a 5 to 7-membered saturated ring optionally containing an additional hetero atom selected from N, O and S, and nontoxic pharmaceutically acceptable salts, physiologically hydrolyzable esters and solvates thereof, which process comprises reacting a compound of the formula

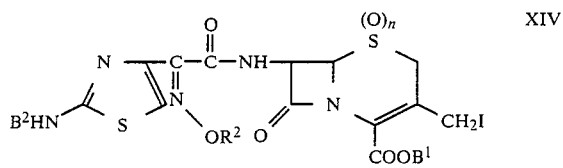

XIV in which $R^2$ is as defined above, $B^1$ is a conventional carboxyl-protecting group, $B^2$ is a conventional amino-protecting group and n is 0 or 1, with a thiazolo[4,5-c]pyridine of the formula

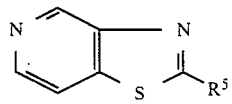

in which $R^5$ is as defined above, to produce a compound of the formula

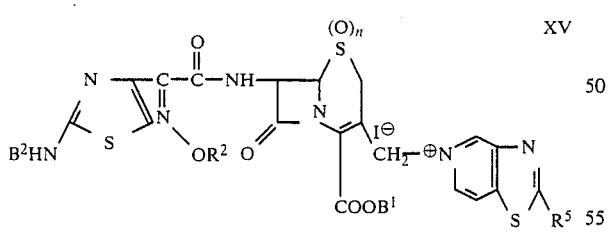

XV and, if n is 1, reducing the sulfoxide by conventional means, and subsequently removing all protecting groups by conventional means.

The reaction is carried out in a non-aqueous organic solvent such as dimethyl sulfoxide, hexamethylphosphoramide, methylene chloride, chloroform, ethyl ether, hexane, ethyl acetate, tetrahydrofuran, acetonitrile and the like, or mixtures of such solvents. The reaction is conveniently carried out at a temperature of from about $-10°$ C. to about $+50°$ C.; we normally prefer to conduct the reaction at room temperature. At least one mole of the tertiary amine should be used per mole of Compound XIV; we normally prefer to utilize from about 50% to 100% excess of the thiazolo[4,5-c]pyridine.

Carboxyl-protecting groups suitable for use as $B^1$ in the above reaction are well-known to those skilled in the art and include aralkyl groups such as benzyl, p-methoxyphenzyl, p-nitrobenzyl and diphenylmethyl(benzhydryl); alkyl groups such as t-butyl; haloalkyl groups such as 2,2,2-trichloroethyl, and other carboxyl-protecting groups described in the literature, e.g. in U.K. Pat. No. 1,399,086. We prefer to utilize carboxyl-protecting groups which are readily removed by treatment with acid. Particularly preferred carboxyl-protecting groups are the benzhydryl and t-butyl moieties.

Amino-protecting groups suitable for use as $B^2$ are also well-known in the art, and include the trityl group and acyl groups such as chloroacetyl, formyl and trichloroethoxycarbonyl. Amino-protecting groups which are readily removed by treatment with acid, e.g. the trityl group, are preferred.

The present invention also provides a process for the preparation of compounds of the formula

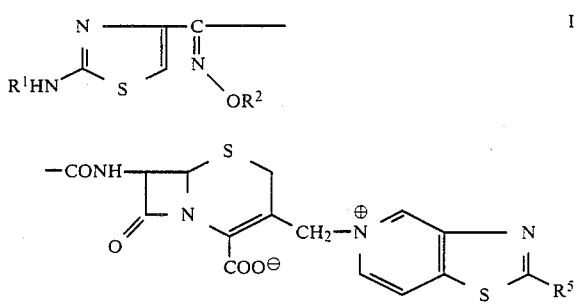

I wherein $R^1$ is hydrogen or a conventional amino-protecting group, $R^2$ is a straight or branched chain alkyl group containing from 1 to 4 carbon atoms, allyl, propargyl, 2-butenyl, 2-butynyl, 3-butenyl, 3-butynyl, cyclo(lower)alkyl or a group of the formula

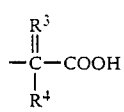

in which $R^3$ and $R^4$ each are independently hydrogen, methyl or ethyl, or $R^3$ and $R^4$, taken together with the carbon atom to which they are attached, may be a cycloalkylidene ring containing from 3 to 5 carbon atoms, and $R^5$ is hydrogen, carboxy, formyl, amino, carbamoyl, (lower)alkylamino, di(lower)alkylamino, guanidino, amidino, (lower)alkyl, (lower)alkoxy, (lower)alkylthio or a group of the formula

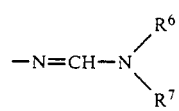

in which $R^6$ and $R^7$ each are independently hydrogen or (lower)alkyl, or when taken together with the nitrogen atom to which they are attached, $R^6$ and $R^7$ represent a 5 to 7-membered saturated ring optionally containing an additional hetero atom selected from N, O and S, or $R^5$ is a group of the formula

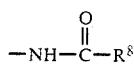

in which $R^8$ is hydrogen, (lower)alkyl, amino(lower)alkyl, (lower)alkoxy, amino, (lower)alkylamino or

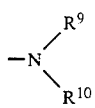

in which $R^9$ and $R^{10}$ are each (lower)alkyl or, when taken together with the nitrogen atom to which they are attached, $R^9$ and $R^{10}$ represent a 5 to 7-membered saturated ring optionally containing an additional hetero atom selected from N, O and S, and nontoxic pharmaceutically acceptable salts, physiologically hydrolyzable esters and solvates thereof, which process comprises acylating a compound of the formula

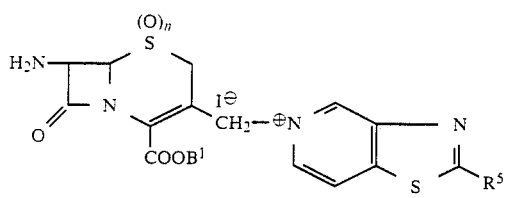

or an N-silyl derivative thereof, in which $B^1$ is hydrogen or a conventional carboxyl-protecting group, n is 0 or 1 and $R^5$ is as defined above, with an acylating derivative of an acid of the formula

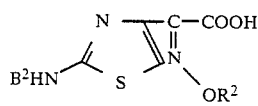

wherein $B^2$ is a conventional amino-protecting group and $R^2$ is as defined above, to produce a compound of the formula

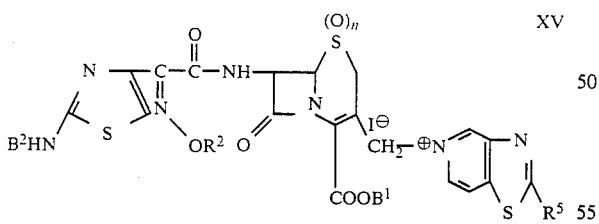

and, if n is 1, reducing the sulfoxide by conventional means, and subsequently removing all protecting groups.

The acylating derivatives of the acid of Formula XVII include the acid halides (and particularly the acid chloride), mixed acid anhydrides (such as the acid anhydrides formed with pivalic acid or a haloformate such as ethyl chloroformate), and activated esters (such as may be formed with N-hydroxybenztriazole in the presence of a condensing agent such as dicyclohexylcarbodiimide). The acylation may also be effected by use of the free acid of Formula XVII in the presence of a condensing agent such as dicyclohexylcarbodiimide, carbonyldiimidazole or an isoxazolium salt. As used herein, the term "acylating derivative" of the acid of Formula XVII includes the free acid itself in the presence of a condensing agent such as described above. The preferred acylating derivative of the acid of Formula XVII is the acid chloride, preferably used in the presence to an acid binding agent (and particularly a tertiary amine acid binding agent such as triethylamine, dimethylaniline or pyridine).

When the acylation is conducted with an acid halide it is possible to utilize an aqueous reaction medium, but a non-aqueous medium is preferred. When acid anhydrides, activated esters, or the free acid in the presence of a condensing agent, are used for the acylation, the reaction medium should be nonaqueous. Particularly preferred solvents for the acylation reaction are halogenated hydrocarbons such as methylene chloride and chloroform, but tertiary amides such as dimethylacetamide or dimethylformamide may be utilized, as well as other conventional solvents such as tetrahydrofuran, acetonitrile and the like.

The acylation reaction may be conducted at a temperature of from about $-50°$ C. to about $+50°$ C. However, it is preferably conducted at or below room temperature and most preferably from about $-30°$ C. to about $0°$ C. It is usually preferred to acylate the compound of Formula XVI with about a stoichiometric amount of the acylating agent of Formula XVII, although a small excess (e.g. 5–25%) of the acylating agent may be utilized.

It is preferable that the compound of Formula XVI be acylated in the form of its N-silyl derivative (when utilizing a non-aqueous reaction medium). This is conveniently done in situ by simply adding a suitable silylating agent (e.g. N,O-bistrimethylsilylacetamide) to the solution of Compound XVI prior to the addition of the acylating agent of Formula XVII. We prefer to utilize about 3 moles of silylating agent per mole of Compound XVI although this is not critical. The silyl compound is readily removed after acylation by the addition of water.

When substituent $R^2$ of the acylating acid of Formula XVII is a group of the formula

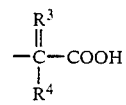

it is preferred that the acylating acid contain a carboxyl-protecting group, i.e. that the acylating acid be utilized in the form

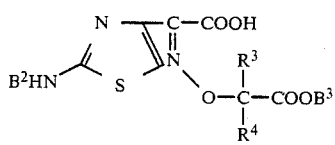

in which $B^2$ is a conventional amino-protecting group as described above, and $B^3$ is a conventional carboxyl-protecting group as described above for $B^1$.

The acylating acids of Formula XVII (and the corresponding precursor esters), including the carboxyl- and amino-protecting derivatives [XVIII] thereof, are known in the art or may be prepared by known procedures. Thus, Compounds IIIa, IIIb and IIIc (shown in Preparation No. 1, below) and Compounds IVa, IVb and IVc (shown in Preparation No. 2, below) are described in Tetrahedron, 34, 2233–2243 (1978), in which they were prepared by a different route. Compounds IVd′ and IVe′, used as starting materials in Preparation No. 11 and Preparation No. 13, respectively, were prepared according to the general procedure described in U.S. Pat. No. 4,258,041 and published United Kingdom Patent Application No. 2,025,398.

The thiazolo[4,5-c]pyridines of the formula

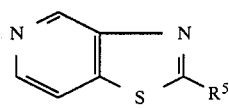

wherein $R^5$ is as described above are known compounds. The preparation of the compounds in which $R^5$ is hydrogen or methyl is described in Pharm. Bull. (Japan), 2, 196–200 (1954) [Chemical Abstracts, 50, 1000i]. The preparation of the compound in which $R^5$ is amino is described in Pharm. Bull. (Japan), 2, 34–37 (1954) [Chemical Abstracts, 50, 335h]. The compound in which $R^5$ is methylthio is described in J. Heterocyclic Chem., 14, 1045 (1977).

When utilizing Reaction Scheme 1 or 2 in which the cephalosporin nucleus is in the form of the 1-oxide (n=1), the 1-oxide is prepared by known procedures such as oxidation with m-chloroperbenzoic acid, peracetic acid, etc. The 1-oxide subsequently may be reduced by known procedures, e.g. reduction of the corresponding alkoxysulfonium salt with iodide ion in an aqueous medium. The alkoxysulfonium salt itself is readily prepared by treatment of the 1-oxide with, for example, acetyl chloride.

As used herein, the terms "(lower)alkyl", "(lower)alkoxy" and "(lower)alkylthio" mean straight or branched chain alkyl, alkoxy and alkylthio groups containing from 1 to 6 carbon atoms, inclusive.

PREPARATION NO. 1

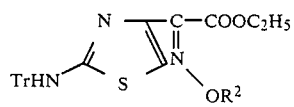

Ethyl (Z)-2-Methoxyimino-2-(2-tritylaminothiazol-4-yl)acetate (IIIa)

A mixture of ethyl (Z)-2-hydroxyimino-2-(2-tritylaminothiazol-4-yl)acetate (II) (5.00 g, 10.9 mmoles), CH₃I (2.04 mL, 32.8 mmoles) and K₂CO₃ (4.54 g, 32.8 mmoles) in dry dimethylsulfoxide (DMSO) (100 mL) was stirred at room temperature overnight and then poured into water (250 mL). The precipitate which formed was collected by filtration, washed with water and dried to give the title compound (5.15 g, quantitative yield). Mp. 115° C. (dec.)

NMR: $\delta^{CDCl_3}$ ppm 1.32 (3H, t), 3.98 (3H, s), 4.30 (2H, q), 6.42 (1H, s), 7.2 (1H, m), 7.25 (15H, s).

Compounds IIIb, IIIc, IIId′, IIIe′ and IIIf were prepared by the general procedure set forth above, but replacing the methyl iodide with the appropriate iodide.

| Compound | $R^2$ | Yield (%) | Mp (°C.) | Literature Mp (°C.) |
|---|---|---|---|---|
| IIIa | methyl | 100 | 115° (dec.) | ca. 120° (dec.)[1] |
| IIIb | ethyl | 67 | 97–98° | * |
| IIIc | allyl | * | * | * |
| IIId′ | —C(CH₃)₂COOtButyl | 100 | 125–126° | 123.5–125[2]; 134[3] |
| IIIe′ | ![]COOtButyl | 68 | 81–83° | not reported[3] |
| IIIf | propargyl | 94 | 70–73° | not reported[4] |

*The ester was hydrolyzed without isolation
[1]Tetrahedron, 34, 2233 (1978)
[2]U.S. Pat. No. 4,258,041
[3]U.S. Pat. No. 4,288,434
[4]U.S. Pat. No. 4,294,960

PREPARATION NO. 2

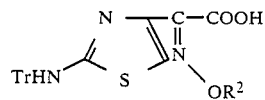

(Z)-2-Methoxyimino-2-(2-tritylaminothiazol-4-yl)acetic acid (IVa)

The ethyl ester IIIa prepared in Preparation No. 1 (6.00 g, 12.7 mmoles) in ethanol (120 mL) was treated with 2N NaOH (12.7 mL) at room temperature overnight. The reaction mixture was adjusted to pH 8 by the addition of powdered dry ice and the solvent was evaporated under reduced pressure. The residue was dissolved in water (100 mL) and the solution was acidified with 1N HCl to pH 2 and then extracted with ethyl acetate (3×50 mL). The combined extracts were washed with a saturated aqueous NaCl solution, dried and evaporated. The residue was crystallized from ethyl acetate-hexane to afford 5.56 g (yield 98%) of the title product. Mp. 138°–143° C. (dec.).

NMR: $\delta^{CDCl_3}$ ppm 3.89 (3H, s), 6.52 (1H, s), 7.2 (15H, s).

Compounds IVb, IVc, IVd′, IVe′ and IVf were prepared by the general procedure set forth above.

| Compound | $R^2$ | Yield (%) | Mp (°C., dec.) | Literature Mp (°C., dec.) |
|---|---|---|---|---|
| IVa | methyl | 98 | 138–143 | ca. 140[1] |
| IVb | ethyl | 85 | 140–145 | not reported[1] |
| IVc | allyl | 66 | 170–178 | ca. 170[1] |
| IVd′ | —C(CH₃)₂COOtButyl | 77 | 174–175 | 152–156[2]; 190[3] |
| IVe′ | ![]COOtButyl | 78 | 163–164 | not reported[2] |
| IVf | propargyl | 88 | 136–138 | — |

[1]Tetrahedron, 34, 2233 (1978)
[2]U.S. Pat. No. 4,258,041
[3]U.S. Pat. No. 4,288,434

PREPARATION NO. 2A

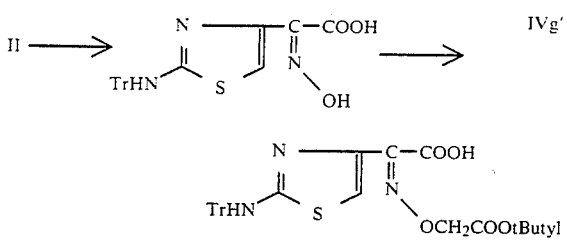

(Z)-2-t-Butoxycarbonylmethoxyimino-2-(2-tritylamino-thiazol-4-yl)-acetic Acid (IVg')

This preparation describes an alternate procedure for the production of compounds of Formula IV.

A mixture of ethyl (Z)-2-hydroxyimino-2-(tritylaminothiazol-4-yl)acetate (II) (23 g, 50 mmoles) and 2N NaOH (50 ml) in dioxane (70 ml) was heated at 50° C. for 1 hour to precipitate the crystalline intermediate product, which was collected by filtration. Yield, 22 g (98%). IR: $\nu_{max}^{nujol}$ 1570, 1520 cm$^{-1}$.

The crystalline sodium salt of the intermediate acid (9.02 g, 20 mmoles) was dissolved in DMF (40 ml) containing a small amount of water (0.4 ml). To the solution was added potassium t-butoxide (2.24 g, 20 mmoles), and the mixture was stirred for an hour at room temperature. To the mixture was added at −5° C. t-butyl bromoacetate (3.90 g, 20 mmoles), and the mixture was stirred at room temperature for an hour. The mixture was poured into water, acidified to pH 3 with dilute hydrochloric acid and extracted with ethyl acetate. The organic extract was washed with water, dried and concentrated to give colorless needles which were collected by filtration to give 6.1 g (56%) of the title compound (IVg').

Mp: 171°–173° C. (dec.) (recrystallized from ethyl acetate)*

*Compound IVg' has been described by R. Bucourt et al. [Eur. J. Med. Chem.—Chimica Therapeutica 16, 307 (1981)]. However, the reported mp (190° C.) is questionable, because it is more than 15° C. higher than that of our crystalline sample obtained by recrystallization.

IR: $\nu_{max}^{KBr}$ cm$^{-1}$ 3250, 1700, 1530.

NMR: $\delta^{CDCl_3}$ ppm 1.50 (9H, s), 4.70 (2H, s), 6.72 (1H, s), 7.30 (15H, s), 8.30 (2H, br, s).

PREPARATION NO. 3

Benzhydryl 3-Hydroxymethyl-7-phenylacetamido-3-cephem-4-carboxylate (VIII)

To a stirred suspension of phosphate buffer (pH 7, 162.5 mL) and wheat bran (20 g, dry) at room temperature was added 7-phenylacetamidocephalosporanic acid sodium salt (5 gm, 12.1 mmoles) in one portion. The progress of the reaction was monitored by HPLC until the hydrolysis was complete (5 hours). The suspension was filtered to remove the wheat bran and the filtrate was cooled to 5°–10° C. for extractive esterification. To the cooled solution was added methylene chloride (32 mL) followed by a 0.5M solution of diphenyldiazomethane in methylene chloride (24 mL). The pH was then adjusted to 3.0 with 28% phosphoric acid. After 1 hour the reaction mixture was allowed to rise to 20° C. Heptane (56 mL) was slowly added and the resulting crystalline title product was recovered by filtration. Yield of the title product was 3.0 gm (50%).

PREPARATION NO. 4

Benzhydryl 7-Amino-3-chloromethyl-3-cephem-4-carboxylate (V)

To a slurry of PCl$_5$ (8.3 g, 40 mmoles) in CH$_2$Cl$_2$ (100 mL) was added pyridine (3.2 g, 40 mmoles) and the mixture was stirred for 20 minutes at 20° C. To the mixture was added benzhydryl 3-hydroxymethyl-7-phenylacetamido-3-cephem-4-carboxylate prepared in Preparation No. 3 (5.1 g, 10 mmoles) with stirring at −40° C., in one portion. The mixture was stirred at −10° C. for 15 minutes and allowed to stand at −10° C. to −15° C. for 7 hours. To the cooled solution (−20° C.) was added propane-1,3-diol (10 mL) and the mixture was allowed to stand at −20° C. for 16 hours and then at room temperature for 20 minutes with stirring. The resulting solution was washed with ice-water (2×20 mL) and saturated aqueous NaCl (10 mL), dried over MgSO$_4$ and concentrated in vacuo. The gummy residue (12 g) was dissolved in a mixture of CHCl$_3$ and n-hexane (2:1), and subjected to chromatography using a silica gel column (200 g) and the same solvent as eluant. Fractions containing the title compound were evaporated in vacuo and the residue triturated with n-hexane to give the title product (2.1 g, 51%), melting at >110° C. (dec.).

IR: $\nu_{KBr}$ 3400, 2800, 1785, 1725 cm$^{-1}$.

UV: $\lambda_{max}^{EtOH}$ 265 nm (E$_{1\,cm}^{1\%}$ 160).

NMR: $\delta_{ppm}^{DMSO-d_6+CDCl_3}$ 3.69 (2H, s), 4.43 (2H, s), 5.09 (1H, d, J=4.5 Hz), 5.24 (1H, d, J=4.5 Hz), 6.87 (1H, s), 7.3 (10H, m).

PREPARATION NO. 5

Benzhydryl 3-Chloromethyl-7-[(Z)-2-methoxyimino-2-(2-tritylaminothiazol-4-yl)acetamido]-3-cephem-4-carboxylate (VIa)

Benzhydryl 7-amino-3-chloromethyl-3-cephem-4-carboxylate prepared in Preparation No. 4 (2.29 g, 5.52 mmoles) in CH$_3$CN (57 mL) was treated with bis(trimethylsilyl)acetamide (BSA, 4.09 mL, 16.6 mmoles) at room temperature for 50 minutes to give a clear solution. To the solution was added an acid chloride solution, which was prepared from (Z)-2-methoxyimino-2-(2-tritylaminothiazol-4-yl)acetic acid (IVa) (2.04 g, 4.60 mmoles) and PCl$_5$ (1.15 g, 5.52 mmoles) in methylene chloride (20 mL). The mixture was stirred at room temperature for 30 minutes, poured into cold water (200 mL) and extracted with ethyl acetate (3×100 mL). The combined extracts were washed with aqueous NaCl, dried and evaporated. The residual syrup (4 g) was chromatographed on a silica gel (150 g) column by eluting with 10:1 and 3:1 mixtures of toluene and ethyl acetate successively. The fractions containing the desired compound were combined and evaporated to afford 2.61 g (68%) of VIa as an amorphous powder.

NMR: $\delta^{CDCl_3}$ ppm 3.50 (2H, s), 4.02 (3H, s), 4.33 (2H, s), 4.98 (1H, d), 5.87 (1H, q), 6.65 (1H, s), 6.90 (1H, s), 7.3 (25H, m).

PREPARATION NO. 6

Benzhydryl 3-Iodomethyl-7-[(Z)-2-methoxyimino-2-(2-tritylaminothiazol-4-yl)acetamido]-3-cephem-4-carboxylate (VIIa)

A mixture of the 3-chloromethyl derivative prepared in Preparation No. 5 (VIa) (1.50 g, 1.79 mmoles) and NaI (1.34 g, 8.93 mmoles) in methyl ethyl ketone (30 mL) was stirred at room temperature for 1 hour. After evaporation of the solvent the residue was dissolved in ethyl acetate (100 mL) and washed with water, aqueous $Na_2S_2O_3$ and aqueous NaCl, dried and evaporated to give the title compound VIIa (1.47 g, 89%) as an amorphous powder.

NMR: $\delta^{CDCl_3}$ ppm 3.55 (2H, ABq), 4.00 (3H, s), 4.25 (2H, s), 4.97 (1H, d), 5.80 (1H, q), 6.65 (1H, s), 6.90 (1H, s), 7.3 (25H, m).

PREPARATION NO. 7

Benzhydryl 3-Chloromethyl-7-[(Z)-2-ethoxyimino-2-(2-tritylaminothiazol-4-yl)acetamido]-3-cephem-4-carboxylate (VIb)

To a solution of (Z)-2-ethoxyimino-2-(2-tritylaminothiazol-4-yl)acetic acid (IVb) (1.095 g, 2.4 mmoles) in dichloromethane (20 mL) was added phosphorus pentachloride (500 mg). After stirring for 1 hour at room temperature, the mixture was added in one portion to an ice-cooled solution of Compound V (1.083 g, 2.4 mmoles) and BSA (1 mL) in dichloromethane (20 mL). After stirring for 0.5 hour the reaction mixture was poured into 10% aqueous $NaHCO_3$ (200 mL) and extracted with $CHCl_3$ (100 mL). The extract was washed with water, dried over $MgSO_4$, and evaporated under reduced pressure. The residue was chromatographed on a silica gel column. Elution with $CHCl_3$ gave VIb as an amorphous powder, 1.76 g (86%).

NMR: $\delta^{CDCl_3}$ ppm 1.40 (3H, t, $CH_2CH_3$), 3.53 (2H, ABq, 2-$CH_2$), 4.37 (2H, s, —$CH_2Cl$), 4.60 (2H, q, —$CH_2CH_3$), 4.90 (1H, d, 6-H), 5.89 (1H, d, 7-H), 6.88 (1H, s, thiazole-H), 6.91 (1H, s, benzhydryl-CH).

PREPARATION NO. 8

Diphenylmethyl 7-[(Z)-2-Ethoxyimino-2-(2-tritylaminothiazol-4-yl)acetamido]-3-iodomethyl-3-cephem-4-carboxylate (VIIb)

A mixture of VIb prepared in Preparation No. 7 (1.07 g, 1.25 mmoles) and NaI (562 mg, 2.75 mmoles) in acetone (20 mL) was stirred for 1 hour. The mixture was filtered and the filtrate was poured into water and extracted with ethyl acetate. The organic layer was washed successively with 5% aqueous $Na_2S_2O_3$, water and saturated aqueous NaCl, dried over $MgSO_4$ and evaporated to give 1.04 g (89%) of Compound VIIb.

NMR: $\delta^{CDCl_3}$ ppm 3.55 (2H, q, 2-$CH_2$), 4.27 (2H, s, $CH_2I$), 5.02 (1H, d, 6-H), 5.87 (1H, d, 7-H), 6.68 (1H, s, thiazole ring H), 6.93 (1H, s, benzhydryl-CH).

PREPARATION NO. 9

Benzhydryl 7-[(Z)-2-Allyloxyimino-2-(2-tritylaminothiazol-4-yl)-acetamido]-3-chloromethyl-3-cephem-4-carboxylate (VIc)

To a suspension of Compound V (1.35 g, 3 mmoles) in methylene chloride (20 mL) was added BSA (1.1 mL, 4.5 mmoles), and the mixture was stirred for 30 minutes at room temperature to become a clear solution. A mixture of (Z)-2-allyloxyimino-2-(2-tritylaminothiazol-4-yl)acetic acid (IVc) (1.40 g, 3.0 mmoles) and phosphorus pentachloride (690 mg, 3.3 mmoles) in methylene chloride (20 mL) was stirred for 15 minutes at room temperature and poured in one portion into the solution of the trimethylsilylated Compound V. The mixture was stirred for 20 minutes at room temperature and diluted with ethyl acetate (200 mL), washed with aqueous sodium bicarbonate and water, dried and evaporated under reduced pressure. The oily residue was purified by silica gel column chromatography (Wako-gel, C-200, 30 g). The column was eluted with chloroform and the fractions containing the desired product were combined. Evaporation under reduced pressure afforded the title compound (VIc) as an amorphous powder, yield 2.32 g (89%). Mp. 100°–115° C. (dec.).

IR: $\nu_{max}^{KBr}$ cm$^{-1}$ 3390, 1790, 1730, 1680, 1530, 1380, 1250, 1160, 1020.

NMR: $\delta^{CDCl_3}$ ppm 3.50 (2H, 2-H), 4.32 (2H, s, 3-$CH_2$), 4.6–6.1 (7H, m, $CH_2CH=CH_2$ and 6,7-H), 6.70 (1H, s, thiazole-H), 6.90 (1H, s, $Ph_2CH$), 7.1–7.6 (25H, m, phenyl protons).

Anal. Calc'd. for $C_{48}H_{40}N_5O_5S_2Cl \cdot 1/3CHCl_3$: C, 64.05; H, 4.45; N, 7.73; S, 7.08; Cl, 7.82. Found: C, 64.13, 63.99; H, 4.61, 4.64; N, 7.50, 7.30; S, 6.85, 6.85; Cl, 7.55, 7.46.

PREPARATION NO. 10

Benzhydryl 7-[(Z)-2-Allyloxyimino-2-(tritylaminothiazol)-4-yl)-acetamido]-3-iodomethyl-3-cephem-4-carboxylate (VIIc)

A mixture of Compound VIc (2.30 g, 2.65 mmoles) and sodium iodide (2 g, 13.3 mmoles) in acetone (15 mL) was stirred for 1 hour at room temperature and then evaporated under reduced pressure. A solution of the oily residue in ethyl acetate (200 mL) was washed with 10% sodium thiosulfate and water, evaporated under reduced pressure to afford Compound VIIc as an amorphous powder, which was used in the subsequent step without further purification. Yield 2.52 g (99%).

PREPARATION NO. 11

Benzhydryl 3-Chloromethyl-7-[(Z)-2-(2-t-butoxycarbonylprop-2-oxyimino)-2-(2-tritylaminothiazol-4-yl)acetamido]-3-cephem-4-carboxylate (VId')

Procedure 1

A mixture of (Z)-2-(2-t-butoxycarbonylprop-2-oxyimino)-2-(2-tritylaminothiazol-4-yl)acetic acid (IVd') (1.94 g, 3.6 mmoles) DCC (742 mg, 3.6 mmoles) and N-hydroxybenztriazole (486 mg, 3.6 mmoles) in tetrahydrofuran (THF) (45 mL) was stirred at room temperature for 45 minutes, during which dicyclohexylurea separated. The dicyclohexylurea was removed by filtration and the filtrate was mixed with V (1.5 g, 3.6 mmoles). The mixture was stirred overnight at room temperature and then evaporated in vacuo. The residual oil was dissolved in $CHCl_3$ (20 mL), washed with saturated aqueous $NaHCO_3$ and saturated aqueous NaCl, dried over $MgSO_4$ and evaporated to dryness. The residue (3.9 g) was dissolved in n-hexane:$CHCl_3$ (1:2) and passed through a silica gel column (40 g) using the same solvent system. Fractions containing the title compound were evaporated in vacuo to give 1.3 g (39%) of VId' melting at >100° C. (dec.).

IR: $\nu_{max}^{KBr}$ cm$^{-1}$ 3390, 1790, 1715, 1690.

UV: $\lambda_{max}^{EtOH}$ nm 240 (E$_{1\ cm}^{1\%}$ 280), 265 (E$_{1\ cm}^{1\%}$ 190).

NMR: $\delta^{CDCl_3}$ ppm 1.45 (9H, s), 1.63 & 1.66 (6H, each s), 3.49 (2H, broad s), 4.34 (2H, s), 4.96 (1H, d, J=4.5 Hz), 5.90 (1H, d-d, J=4.5 & 7.5), 6.66 (1H, s), 6.86 (1H, s), 7.0–7.5 (25H, m), 8.23 (1H, d, J=7.5 Hz).

Procedure 2

A solution of V (1.86 g, 4.49 mmoles) in CH$_3$CN (46.5 mL) was treated with BSA (3.33 mL, 13.5 mmoles) at room temperature for 50 minutes to give a clear solution. To the solution was added an acid chloride solution which had been prepared from IVd' (2.56 g, 4.49 mmoles) and PCl$_5$ (1.12 g, 5.38 mmoles) in methylene chloride (26 mL). The mixture was stirred at room temperature for 30 minutes, poured into cold water (100 mL) and extracted with ethyl acetate (3×50 mL). The combined extracts were washed with aqueous NaCl, dried and evaporated. The residual syrup (5 g) was chromatographed on a silica gel (100 g) column by eluting with 10:1 mixture of toluene and ethyl acetate. The fractions containing the desired compound were combined and evaporated to afford 2.84 g (65%) of VId'.

PREPARATION NO. 12

Benzhydryl 7-[(Z)-2-(2-t-Butoxycarbonylprop-2-oxyimino)-2-(2-tritylaminothiazol-4-yl)acetamido]-3-iodomethyl-3-cephem-4-carboxylate (VIId')

A mixture of VId' (500 mg, 0.53 mmole) and NaI (240 mg, 1.6 mmoles) in acetone (3 mL) was stirred for 2 hours at room temperature and then evaporated in vacuo. To the residue were added CH$_2$Cl$_2$ (20 mL) and water (10 mL). The organic layer was washed with 10% w/v sodium thiosulfate (5 mL) and aqueous NaCl (5 mL), dried over MgSO$_4$ and evaporated to dryness to give 540 mg (99%) of VIId' as an amorphous powder melting at 106° C. (dec.).

IR: $\nu_{max}^{KBr}$ cm$^{-1}$ 3350, 1790, 1690.
UV: $\lambda_{max}^{EtOH}$ nm 240 (E$_1$ $_{cm}$$^{1\%}$ 270), 265 (E$_1$ $_{cm}$$^{1\%}$ 190).
NMR: $\delta^{CDCl_3}$ ppm 1.44 (9H, s), 1.65 (6H, s), 3.54 (2H, ABq), 4.28 (2H, s), 4.98 (1H, d, J=4.5 Hz), 5.85 (1H, d-d, J=4.5 & 7.5 Hz), 6.70 (1H, s), 6.90 (1H, s), 7.1–7.5 (25H, m).

PREPARATION NO. 13

Diphenylmethyl 7-[(Z)-2-(1-t-Butoxycarbonylcyclobut-1-oxyimino)-2-(2-tritylaminothiazol-4-yl)acetamido]-3-chloromethyl-3-cephem-4-carboxylate (VIe')

Phosphorus pentachloride (1.46 g, 7 mmoles) was added to a suspension of (Z)-2-(1-t-butoxycarbonylcyclobut-1-oxyimino)-2-(2-tritylaminothiazol-4-yl)acetic acid [IVe'] (4.09 g, 7 mmoles) in 70 mL of dry methylene chloride, and the mixture was stirred for 1 hour at room temperature. The acid chloride solution was added at −20° C. to a solution of silylated 7-ACA ester, which was prepared by adding BSA (5.6 mL, 21 mmoles) to a stirred suspension of benzhydryl 7-amino-3-chloromethyl-3-cephem-4-carboxylate hydrochloride [V] (3.16 g, 7 mmoles) in dry methylene chloride (70 mL). The mixture was stirred for 20 minutes at −10° C. and then at room temperature for 40 minutes. The reaction mixture was evaporated and diluted with ethyl acetate (300 mL), and the organic layer was washed with 5% aqueous sodium bicarbonate, water and a saturated sodium chloride solution. After drying over sodium sulfate, the solvent was evaporated and the residue was purified by silica gel column chromatography (Wako gel C-200, 60 g); elution with chloroform. The fractions containing the desired product were combined and evaporated to obtain 5.88 g (86%) of VIe' as a yellow powder.

IR: $\nu_{max}^{KBr}$ cm$^{-1}$ 1790, 1725, 1690, 1525.
UV: $\lambda_{max}^{EtOH}$ nm 254 nm (E$_1$ $_{cm}$$^{1\%}$=214).

PREPARATION NO. 14

Diphenylmethyl 7-[(Z)-2-(1-t-Butoxycarbonylcyclobut-1-oxyimino)-2-(2-tritylaminothiazol-4-yl)acetamido]-3-iodomethyl-3-cephem-4-carboxylate (VIIe')

To a stirred solution of VIe' (5.4 g, 5.5 mmoles) in acetone (108 mL) was added sodium iodide (2.48 g, 16.5 mmoles), and the mixture was stirred at room temperature for 3 hours. The reaction mixture was then filtered and evaporated to dryness, and the residue was dissolved in ethyl acetate (200 mL). The solution was washed with water (100 mL), 10% w/v sodium thiosulfate (40 mL) and saturated sodium chloride (3×70 mL). After drying over magnesium sulfate, the solvent was removed under reduced pressure to give 5.38 g (91%) of VIIe' as a yellow powder.

IR: $\nu_{max}^{KBr}$ cm$^{-1}$ 1790, 1725, 1690, 1525.
UV: $\lambda_{max}^{EtOH}$ nm 254 (E$_1$ $_{cm}$$^{1\%}$=184).
NMR: $\delta^{CDCl_3}$ ppm 1.45 (9H, s), 1.8–2.8 (6H, m), 3.52 (2H, ABq), 4.25 (2H, s), 4.98 (1H, d, J=5.3 Hz), 5.87 (1H, dd, J=9 & 5.3 Hz), 6.70 (1H, s), 6.88 (1H, s), 6.90 (1H, s), 7.28 (25H, s), 8.41 (1H, d, J=9 Hz).

PREPARATION NO. 15

Diphenylmethyl 3-chloromethyl-7-[(Z)-2-propargyloxyimino-2-(2-tritylaminothiazol-4-yl)acetamido]-3-cephem-4-carboxylate [VI-f]

Phosphorus pentachloride (910 mg) was added to a solution of (Z)-2-propargyloxyimino-2-(2-tritylaminothiazol-4-yl)acetic acid (IV-f) (1.7 g, 3.6 mmoles) in dichloromethane (30 ml). After stirring for 1 hour at room temperature, the mixture was added in one portion to an ice-cooled solution of (V) (1.98 g, 4.4 mmoles) and N,O-bis(trimethylsilyl)acetamide (1.5 ml) in dichloromethane (30 ml). After stirring for 1 hour, the reaction mixture was poured into 10% aqueous NaHCO$_3$ (300 ml) and extracted with ethyl acetate (300 ml). The extract was washed with water, dried over MgSO$_4$ and evaporated under reduced pressure. The residue was chromatographed on a silica gel column. Elution with CHCl$_3$ gave the title compound [VI-f] as an amorphous powder weighing 2.1 g (66%).

NMR: $\delta^{CDCl_3}$ ppm 2.45 (1H, t, CH), 3.53 (2H, d, 2-CH$_2$), 4.37 (2H, s, —CH$_2$Cl), 4.83 (2H, d, O—CH$_2$C≡CH), 5.03 (1H, d, 6-H), 5.90 (1H, q, 7-H), 6.70 (1H, s, thiazole-H), 6.92 (1H, s, benzhydryl-CH).

PREPARATION NO. 16

Diphenylmethyl 7-[(Z)-2-propargyloxyimino-2-(2-tritylaminothiazol-4-yl)acetamido]-3-iodomethyl-3-cephem-4-carboxylate [VII-f]

A mixture of diphenylmethyl 3-chloromethyl-7-[(Z)-2-propargyloxyimino-2-(2-tritylaminothiazol-4-yl)acetamido]-3-cephem-4-carboxylate (VI-f) (2.0 g, 2.3 mmoles) and NaI (1.04 g, 6.9 mmoles) in acetone (40 ml) was stirred for 1 hour. The mixture was filtered and the filtrate was poured into water and extracted with ethyl acetate. The organic layer was washed with 5% aqueous Na$_2$S$_2$O$_3$, water and a saturated aqueous NaCl, successively. It was then dried over MgSO₄ and evaporated to give 2.2 g (98%) of the title compound [VII-f].

NMR: $\delta^{CDCl_3}$ ppm 2.45 (1H, t, CH), 3.53 (2H, d, 2-CH₂), 4.25 (2H, s, CH₂I), 4.83 (2H, d, O—CH₂), 5.0 (1H, d, 6-H), 5.80 (1H, q, 7-H), 6.70 (1H, s, thiazole-H), 6.92 (1H, s, benzhydryl-CH).

PREPARATION NO. 17

Benzhydryl 7-[(Z)-2-t-butoxycarbonylmethoxyimino-2-(2-tritylaminothiazol-4-yl)acetamido]-3-chloromethyl-3-cephem-4-carboxylate (VIg')

To an ice-cooled solution of (Z)-2-t-butoxycarbonylmethoxyimino-2-(tritylaminothiazol-4-yl)acetic acid (IVg') (2.71 g, 5 mmoles) in CH₂Cl₂ (20 ml) was added PCl₅ (1.24 g, 6 mmoles), and the solution was stirred for 20 minutes at room temperature. The acid chloride solution was added under ice-cooling to a solution of the silylated 7-ACA ester, which was prepared by adding bis(trimethylsilyl)acetamide (BSA, 3.7 ml, 15 mmoles) to a stirred suspension of benzhydryl 7-amino-3-chloromethyl-3-cephem-4-carboxylate hydrochloride (V) (2.25 g, 5 mmoles) in CH₂Cl₂ (20 ml). The reaction mixture was stirred at room temperature for 30 minutes, diluted with ethyl acetate (200 ml) and washed with an aqueous NaHCO₃ solution and water. After drying over Na₂SO₄, the solution was evaporated and the residue was purified by silica gel chromatography (Wako gel C-200, 60 g). The desired fractions, eluted by CHCl₃, were combined and concentrated to give 3.16 g (67%) of the title compound VIg'.

IR: $\nu_{max}^{KBr}$ cm⁻¹ 1780, 1720, 1670, 1520.

NMR: $\delta^{CDCl_3}$ ppm 1.40 (9H, s), 3.47 (2H, s), 4.33 (2H, s), 4.70 (2H, s), 5.00 (1H, d, 5 Hz), 5.85 (1H, dd, 5 & 8 Hz), 6.76 (1H, s), 6.92 (1H, s), 7.30 (25H, m), 8.70 (1H, d, 8 Hz).

PREPARATION NO. 18

Benzhydryl 7-[(Z)-2-t-butoxycarbonylmethoxyimino-2-(2-tritylaminothiazol-4-yl)acetamido]-3-iodomethyl-3-cephem-4-carboxylate (VIIg')

To a solution of VIg' (3.16 g, 3.36 mmoles) in acetone (50 ml) was added sodium iodide (3 g, 20 mmoles) and the solution was allowed to stand at room temperature for 30 minutes. The reaction mixture was evaporated to dryness and the residue was dissolved in ethyl acetate (100 ml), washed with water and 10% w/v sodium thiosulfate. After drying over anhydrous Na₂SO₄, the solution was evaporated under reduced pressure to give 3.57 g of the title compound (VIIg').

IR: $\nu_{max}^{nujol}$ cm⁻¹ 1785, 1720, 1520.

NMR: $\delta^{CDCl_3}$ ppm 1.45 (9H, s), 3.54 (2H, d, 3 Hz), 4.24 (2H, s), 4.72 (2H, s), 5.00 (1H, d, 4 Hz), 5.84 (1H, dd, 4 and 8 Hz), 6.78 (1H, s), 6.92 (1H, s), 7.0–7.6 (25H, m).

EXAMPLE 1

7-[(Z)-2-(2-Aminothiazol-4-yl)-2-methoxyiminoacetamido]-3-{(5-thiazolo[4,5-c]pyridinio)methyl}-3-cephem-4-carboxylate (Ia)

A mixture of benzhydryl 3-iodomethyl-7-[(Z)-2-methoxyimino-2-(2-tritylaminothiazol-4-yl)acetamido]-3-cephem-4-carboxylate [VIIa] (1.50 g, 1.61 mmoles) and thiazolo[4,5-c]-pyridine (300 mg, 2.20 mmoles) in dry dimethylsulfoxide (DMSO) (7.5 mL) was stirred at room temperature for 1 hour. The reaction mixture was diluted with ethyl acetate (20 mL), washed with water (5 mL), dried and evaporated to dryness. To a solution of the residue in CHCl₃ (5 mL) was added ether (50 mL) to give the quaternized blocked cephalosporin [XIIIa] (1.7 g), which was collected by filtration and treated with 90% trifluoroacetic acid [TFA] (17 mL) at room temperature for 1 hour. After evaporation of the solvent, the residue was triturated with ether, filtered and dissolved in CH₃OH (2 mL). The solution was treated with 1M sodium 2-ethylhexanoate [SEH] in ethyl acetate (3.2 mL) at room temperature for 30 minutes to afford 774 mg of the crude title compound (Ia), which was purified by HPLC (Column, Lichrosorb RP-18, 8×300 mm; eluted with 0.01M ammonium phosphate buffer, pH 7.2—15% CH₃OH) and HP-20 column chromatography (3×30 cm, washed with 1 L of water and eluted with 700 mL of 30% CH₃OH). The fractions containing the desired product were collected, concentrated and lyophilized to afford 180 mg (22%) of the title compound (Ia) as a colorless powder, mp 165° C. (dec.).

IR: $\nu_{max}^{KBr}$ cm⁻¹ 3400, 1770, 1615.

UV: $\lambda_{max}^{phosphate\ buffer,\ pH\ 7}$ nm($\epsilon$) 225 (43400), 261 (21000).

NMR: $\delta^{D_2O}$ ppm 3.53 (2H, ABq), 4.03 (3H, s), 5.36 (1H, d, J=4.8 Hz), 5.88 (1H, d), 6.94 (1H, s), 8.9 (2H, m), 9.81 (1H, s), 9.88 (1H, s).

EXAMPLE 2

7-[(Z)-2-(2-Aminothiazol-4-yl)-2-methoxyiminoacetamido]-3-{(5-thiazolo[4,5-c]pyridino)methyl}-3-cephem-4-carboxylate (Ia)

A mixture of benzhydryl 3-iodomethyl-7-[(Z)-2-methoxyimino-2-(2-tritylaminothiazol-4-yl)acetamido]-3-cephem-4-carboxylate [VIIa] (18.6 g, 0.02 mole) and thiazolo[4,5-c]-pyridine (3.54 g, 0.026 mole) in 60 mL of dry DMSO was stirred at room temperature for one hour. The reaction mixture was diluted with 300 mL of chloroform, washed with 200 mL of water and dried over anhydrous MgSO₄. The chloroform solution was treated with active carbon (2 g) and filtered. The filtrate was concentrated to 30 mL and diluted with 1 L of ether. The resulting precipitate was collected by filtration and washed with ether to give 23 g of the blocked cephalosporin [XIIIa], which was deblocked by stirring with 100 mL of 90% trifluoroacetic acid at room temperature for one hour. The mixture was concentrated to 10 mL below 30° C. and poured into 1 L of ether. The resulting solid was collected by filtration and dissolved in 50 mL of methanol. Insolubles were removed by filtration. To the filtrate was added 40 mL (0.04 mole) of SEH in ethyl acetate with shaking and the mixture was diluted with 1 L of ethyl acetate. The precipitate which separated was collected by filtration, washed with ethyl acetate and dried in vacuo over P₂O₅ to give 11 g of crude title compound (Ia). The crude product was dissolved in 1500 mL of water and insoluble material (4.2 g) was removed by filtration. The filtrate was evaporated to dryness to give an oily residue which was dissolved in 300 mL of water at 30°–35° C. The solution was filtered, concentrated to 50 mL and lyophilized to give an amorphous powder, which was dissolved in 30 mL of 5% methanol and chromatographed by preparative HPLC (Waters System 500, PrepPAK-500/C₁₈). Fractions containing the desired product were collected and concentrated to 30 mL and lyophilized to give 3.64 g (34%) of the purified title compound (Ia). Mp ca. 170° C. (gradually dec.).

A more soluble form of Compound Ia was prepared as follows. A stirred mixture of Compound Ia prepared in the above procedure (250 mg) and distilled water (1.0 mL) was not completely soluble (indicated pH was 4.3). Powdered NaHCO₃ was added in small portions, with stirring. A clear solution was obtained after adding 5.0 mg of NaHCO₃ and the indicated pH then was 6.0. After filtration through a Millipore membrane filter to remove they insoluble impurities, the filtrate was lyophilized to give 245 mg of a water-soluble form of Compound Ia, mp 165° C. Estimated purity 80% (by HPLC). The sample was completely soluble in water to give a 25% solution.

IR: $\nu_{max}^{KBr}$ cm$^{-1}$ 3400, 1770, 1615.

UV: $\lambda_{max}^{phosphate\ buffer,\ pH\ 7}$ nm($\epsilon$) 225 (44200), 260 (21600).

Anal. Calc'd for $C_{20}H_{17}N_7O_5S_3 \cdot 3H_2O$: C, 41.02; H, 3.96; N, 16.74. Found: C, 40.92; H, 3.18; N, 16.61.

EXAMPLE 3

7-[(Z)-2-(2-Aminothiazol-4-yl)-2-ethoxyiminoacetamido]-3-{(5-thiazolo[4,5-c]pyridino)methyl}-3-cephem-4-carboxylate (Ib)

A mixture of benzhydryl 7-[(Z)-2-ethoxyimino-2-(2-tritylaminothiazol-4-yl)acetamido]-3-iodomethyl-3-cephem-4-carboxylate [VIIb] (517 mg, 0.5 mmole) and thiazolo[4,5-c]-pyridine (88 mg, 0.65 mmole) in DMSO (5 mL) was stirred for 1 hour at room temperature. The reaction mixture was diluted with CHCl₃ (40 mL), washed with water and dried over MgSO₄. The filtrate was evaporated in vacuo and the residue was washed with ether and dissolved in 90% aqueous TFA. After standing for 1 hour at room temperature, the reaction mixture was concentrated in vacuo. The addition of ether to the concentrate resulted in separation of the product, which was collected by filtration and dissolved in a small amount of CH₃OH. The solution was chromatographed on an HP-20 column (50 mL) by eluting with 30% aqueous CH₃OH. The eluate was lyophilized to give 133 mg (47%) of the title compound (Ib) as an amorphous powder. Mp >160° C. (dec.).

UV: $\lambda_{max}^{phosphate\ buffer,\ pH\ 7}$ nm($\epsilon$) 226 (44000), 258 (20000).

NMR: $\delta^{D_2O}$ ppm 1.38 (3H, t), 3.57 (2H, q), 4.32 (2H, q), 5.37 (1H, d), 5.70 (2H, d), 5.93 (1H, d), 6.98 (1H, s), 8.70–9.0 (2H, m), 9.80–9.92 (2H, m).

EXAMPLE 4

7-[(Z)-2-Allyloxyimino-2-(2-aminothiazol-4-yl)acetamido]-3-{(5-thiazolo[4,5-c]pyridino)methyl}-3-cephem-4-carboxylate (Ic)

A mixture of benzhydryl 7-[(Z)-2-allyloxyimino-2-(2-tritylaminothiazol-4-yl)acetamido]-3-iodomethyl-3-cephem-4-carboxylate [VIIc] (478 mg, 0.5 mmole) and thiazolo[4,5-c]-pyridine (108 mg, 0.8 mmole) in DMSO (1 mL) was stirred for 50 minutes at room temperature. The mixture was diluted with chloroform (100 mL), washed with water and evaporated under reduced pressure. The oily residue was triturated with ether and collected by filtration (610 mg). A mixture of this material and TFA (3 mL) was allowed to stand at room temperature for 2 hours and diluted with ether to precipitate the trifluoroacetate of the title compound (465 mg), which was collected by filtration and chromatographed on a column of HP-20 (1.8×15 cm). The column was eluted with water (1 L) and 30% aqueous methanol (1 L). The methanolic eluate was evaporated under reduced pressure and the residue was lyophilized to give the crude title compound (58 mg), which was purified by HPLC [Column, Lichrosorb RP-18; Mobile phase, 0.01M NH₄H₂PO₄ (pH 7):CH₃OH=75:25]. The eluate of the HPLC was chromatographed on a column of HP-20 (1.8×10 cm). The column was eluted with water (500 mL) and 50% aqueous methanol (500 mL). The methanolic eluate was evaporated under reduced pressure and the residue was lyophilized to give 31 mg (11%) of the title compound (Ic) as a pale yellow powder. Mp >160° C. (dec.).

IR: $\nu_{max}^{KBr}$ cm$^{-1}$ 3600-3000, 1770, 1660, 1535.

UV: $\lambda_{max}^{phosphate\ buffer,\ pH\ 7}$ nm($\epsilon$) 225 (44000), 260 (21300).

NMR: $\delta^{D_2O+NaHCO_3}$ ppm 3.50 (1H, d, 18 Hz, 2-H), 3.85 (1H, d, 18 Hz, 2-H), 5.95 (1H, d, 4 Hz, 7-H), 7.00 (1H, s, thiazole-H), 8.90 (2H, m, thiazolopyridine-H), 9.85 (1H, s, thiazolopyridine-H), 9.93 (1H, s, thiazolopyridine-H).

EXAMPLE 5

7-[(Z)-2-(2-Aminothiazol-4-yl)-2-(2-carboxyprop-2-oxyimino)-acetamido]-3-{(5-thiazolo[4,5-c]pyridino)methyl}-3-cephem-4-carboxylate (Id)

To a stirred solution of diphenylmethyl 7-[(Z)-2-t-butoxycarbonylprop-2-oxyimino)-2-(2-tritylamino-thiazol-4-yl)-acetamido]-3-iodomethyl-3-cephem-4-carboxylate [VIId'] (700 mg, 0.66 mmole) in 3 mL of DMSO, was added thiazolo[4,5-c]pyridine (115 mg, 0.84 mmole) in two portions and the mixture was stirred for 1.25 hours at room temperature. The reaction mixture was diluted with ether (150 mL) to separate an oily product, which was washed again with ether. The residue was dissolved in methylene chloride (100 mL) and the solution was filtered and evaporated to give 655 mg of the blocked product [XIIId']. The yellow product (630 mg) was suspended in anisole (1 mL) and, with ice cooling, was treated with a mixture of TFA (10 mL) and water (0.5 mL). The mixture was stirred for 20 minutes with ice cooling and then for 1 hour at room temperature. After evaporation of the mixture below 30° C., the residue was triturated with isopropyl ether (50 mL). The precipitate was collected by filtration, and dried under reduced pressure to obtain 485 mg of crude title compound as a yellow powder. The crude product (480 mg) was dissolved in a small volume of aqueous sodium bicarbonate and purified by HPLC (Column, Lichrosorb RP-18; mobile phase, water). The desired fractions were combined (ca. 90 mL) and acidified to pH 2 with dilute hydrochloric acid. The acidified solution was passed through an HP-20 column (50 mL) and washed with water (200 mL). The fractions eluted with 40% methanol were combined, concentrated and lyophilized to afford 154 mg of pale yellow amorphous powder, which was slightly soluble in water. Microanalysis showed that this was the free acid of the title compound (Id). Mp >180° C. (dec.).

IR: $\nu_{max}^{KBr}$ cm$^{-1}$ 1770, 1660, 1610, 1540.

UV: $\lambda_{max}^{phosphate\ buffer,\ pH\ 7}$ nm($\epsilon$) 225 (45900), 260 (22200).

NMR: $\delta^{DMSO-d_6}$ ppm 1.40 (6H, s), 5.10 (1H, d, J=4 Hz), 5.33 (1H, br, s), 5.70 (1H, br, s), 5.80 (1H, m), 6.66 (1H, s), 9.14 (2H, ABq), 9.88 (1H, s), 10.33 (1H, br, s).

Anal. Calc'd for $C_{23}H_{21}N_7O_7S_3 \cdot 2.5H_2O$: C, 42.59; H, 4.04; N, 15.11; S, 14.83. Found: C, 42.69, 42.58; H, 3.49, 3.47; N, 15.15, 15.08; S, 15.01.

Atomic absorption analysis: Na, 0.01.

The free acid of Compound Id (100 mg) was dissolved in a small volume of aqueous sodium bicarbonate and subjected to HPLC (Column, Lichrosorb RP-18; mobile phase, water). The eluate containing the desired product which was concentrated and lyophilized to give 30 mg of the sodium salt of Id as a pale yellow amorphous powder, which was more than 25% soluble in water. Mp 178°–196° C. (dec.).

IR: $\nu_{max}^{KBr}$ cm$^{-1}$ 1770, 1605, 1540.

UV: $\lambda_{max}^{phosphate\ buffer,\ pH\ 7}$ nm($\epsilon$) 225 (42400), 260 (21000).

NMR: $\delta^{D_2O}$ ppm 1.57 (6H, s), 3.55 (2H, ABq), 5.38 (1H, d, J=4.5 Hz), 5.70 (2H, ABq), 5.93 (1H, d, J=4.5 Hz), 6.94 (1H, s), 8.89 (2H, ABq), 9.83 (1H, s), 9.92 (1H, s).

Anal. Calc'd for $C_{23}H_{20}N_7O_7S_3Na \cdot 3H_2O$: C, 40.64; H, 3.86; N, 14.43; S, 14.15; Na, 3.38. Found: C, 40.54, 40.65; H, 3.52, 3.48; N, 14.35, 14.41; S, 14.16; Na, 3.35.

EXAMPLE 6

7-[(Z)-2-(2-Aminothiazol-4-yl)-2-(2-carboxyprop-2-oxyimino)-acetamido]-3-{(5-thiazolo[4,5-c]pyridinio)-methyl}-3-cephem-4-carboxylate (Id)

A solution of diphenylmethyl 7-[(Z)-(2-t-butoxycarbonylprop-2-oxyimino)-2-(2-tritylaminothiazol-4-yl)acetamido]-3-iodomethyl-3-cephem-4-carboxylate [VIId'] (9.0 g, 8.5 mmoles) and thiazolo[4,5-c]pyridine (1.5 g, 11 mmoles) in dimethylsulfoxide (38 mL) was stirred at room temperature for 1 hour. The reaction mixture was poured into ether (500 mL) and, after decantation, the oily precipitate was dissolved in chloroform (300 mL). The solution was washed with water (2×250 mL), dried over $Na_2SO_4$ and evaporated in vacuo. The oily residue was triturated with ether to give a yellow solid (8.5 g) which was treated with a mixture of anisole (4.3 mL), water (2.2 mL) and TFA (43 mL) at 0° C. for 5 minutes and then at room temperature for 1 hour. The reaction mixture was evaporated and the oily residue was triturated with isopropyl ether to give 7.49 g of the crude title product (estimated purity 42%). The product was dissolved in aqueous NaHCO$_3$ and purified by HPLC (Waters System 500, prepPack-S-500/C$_{18}$, mobile phase H$_2$O), yielding 1.55 g (36%) of the title compound (Id) as its Na salt, which was more than 25% soluble in water. Mp >180° C. (dec.).

IR: $\nu_{max}^{KBr}$ cm$^{-1}$ 3400, 1770, 1660, 1610, 1540, 1480, 1400, 1360, 1190, 1150, 1120, 1085, 1040, 970, 920, 840, 790, 760.

UV: $\lambda_{max}^{phosphate\ buffer,\ pH\ 7}$ nm($\epsilon$) 225 (45700), 260 (22000).

NMR: $\delta^{D_2O}$ ppm 1.47 (6H, s), 3.20 & 3.70 (1H each, d, J=18 Hz), 5.26 (1H, d, J=4.5 Hz), 5.40 and 5.75 (1H each, d, J=15 Hz), 5.78 (1H, d, J=4.5 Hz), 6.68 (1H, s), 8.68 (1H, d, J=7.5 Hz), 8.88 (1H, d, J=7.5 Hz), 9.68 (1H, s), 9.84 (1H, s).

EXAMPLE 7

7-[(Z)-2-(2-Aminothiazol-4-yl)-2-(1-carboxycyclobut-1-oxyimino)-acetamido]-3-{(5-thiazolo[4,5-c]pyridinio)-methyl}-3-cephem-4-carboxylate (Ie)

To a solution of diphenylmethyl 7-[(Z)-2-(1-t-butoxycarbonylcyclobut-1-oxyimino)-2-(2-tritylaminothiazol-4-yl)-acetamido]-3-iodomethyl-3-cephem-4-carboxylate [VIIe'] (482 mg, 0.45 mmole) in 2 mL of DMSO was added thiazolo[4,5-c]pyridine (68 mg, 0.5 mmole) in one portion. The mixture was stirred for 45 minutes at room temperature. The reaction mixture was then diluted with ether (50 mL) and the precipitated oil was triturated in ether (4×50 mL). The precipitate was mixed with anisole (0.5 mL), trifluoroacetic acid (5 mL) and water (0.5 mL), and the mixture stirred with ice cooling for 30 minutes and at room temperature for 1 hour, and then was concentrated under reduced pressure (<30° C.). The residue was triturated with isopropyl ether (100 mL), and the resulting precipitate was collected by filtration to afford 395 mg of crude title compound, as a yellow powder. The crude product (387 mg) was purified on an HP-20 column (100 mL). The eluate containing desired product, which was eluted with 50% methanol, was concentrated and lyophilized to give 80 mg (31%) of the title product (Ie) as a pale yellow amorphous powder. Mp >170° C. (dec.).

IR: $\nu_{max}^{KBr}$ cm$^{-1}$ 1775, 1663, 1620, 1540.

UV: $\nu_{max}^{phosphate\ buffer,\ pH\ 7}$ nm($\epsilon$) 224.5 (46000), 259 (22500).

NMR: $\delta^{D_2O(NaHCO_3)}$ ppm 1.8–2.7 (6H, m), 3.56 (2H, ABq), 5.42 (1H, d, J=4.5 Hz), 5.70 (2H, ABq), 5.94 (1H, d, J=4.5 Hz), 6.93 (1H, s), 8.90 (2H, ABq), 9.82 (1H, s), 9.94 (1H, s).

EXAMPLE 8

7-[(Z)-2-(2-Aminothiazol-4-yl)-2-(propargyloxyimino)acetamido]-3-(2-amino-5-thiazolo[4,5-c]pyridinio)methyl-3-cephem-4-carboxylate (If)

A mixture of diphenylmethyl 7-[(Z)-2-(propargyloxyimino)-2-(2-tritylaminothiazol-4-yl)acetamido]-3-iodomethyl-3-cephem-4-carboxylate [VIIf] (580 mg, 0.61 mmole), and 2-aminothiazolo[4,5-c]pyridine (94 mg, 0.62 mmole) in 2.5 ml of dry DMSO was stirred at room temperature for 30 minutes. The mixture was diluted with ethyl acetate (50 ml), and the resulting precipitate was collected by filtration and dissolved in CHCl$_3$—CH$_3$OH (4:1, 50 ml). The solution was filtered and evaporated, and the residue was triturated with iso-propyl ether. The precipitate was collected by filtration to give 404 mg of crude quaternary salt [XIIIf], which was mixed with anisole (0.4 ml) and treated with 95% TFA (5 ml) under ice cooling. The solution was stirred at room temperature for an hour and then evaporated. The residue was triturated with iso-propyl ether and the resulting precipitate was collected by filtration to afford 282 mg of crude product If, which was purified on an HP-20 column (50 ml). Elution with water (150 ml), 30% aqueous CH$_3$OH (200 ml) and 50% aqueous CH$_3$OH (200 ml) gave 39 mg (5%) of If as pale yellow powder. Mp. 138°~150° C. (dec.). Estimated purity by HPLC: 45%.

IR: $\nu_{max}^{KBr}$ cm$^{-1}$ 1770, 1660(sh), 1625, 1530.

UV: $\nu_{max}^{Phosphate\ buffer\ (pH\ 7)}$ nm($\epsilon$) 247 (45800).

EXAMPLE 9

7-[(Z)-2-(2-Aminothiazol-4-yl)-2-(carboxymethoxyimino)acetamido]-3-(2-amino-5-thiazolo[4,5-c]pyridinio)methyl-3-cephem-4-carboxylate (Ig)

A mixture of diphenylmethyl 7-[(Z)-2-(t-butoxycarbonylmethoxyimino)-2-(tritylaminothiazol-4-yl)acetamido]-3-iodomethyl-3-cephem-4-carboxylate [VIIg'] (600 mg, 0.58 mmole) and 2-aminothiazolo[4,5-c]pyridine (88 mg, 0.58 mmole) in 2 ml of dry DMSO was stirred at room temperature for an hour, and then diluted with ethyl acetate (50 ml). The resulting precipitate was collected by filtration to give 378 mg of quaternary salt [XIIIg'], which was mixed with anisole (0.5 ml). To the mixture was added 5 ml of 90% TFA under ice cooling, and the resulting solution was stirred at room temperature for an hour. After evaporation, the residue was triturated with iso-propyl ether. The yellow precipitate was collected by filtration to afford 372 mg of powder Ig. The crude product was dissolved in a small volume of CH$_3$OH, and the solution was adsorbed on a column of HP-20 (50 ml). Elution with water (200 ml), 30% aqueous CH$_3$OH (200 ml) and 50% aqueous CH$_3$OH (300 ml) gave 121 mg (64%) of the title compound [Ig] as a yellow powder. Mp. 146°~158° C. (dec.). Estimated purity by HPLC: 75%.

IR: $\nu_{max}^{KBr}$ cm$^{-1}$ 1770, 1630, 1540.

UV: $\nu_{max}^{Phosphate\ buffer}$ nm($\epsilon$) 247 (56800).

NMR: $\delta_{ppm}^{D2O+NaHCO3}$ 3.48 (2H, ABq), 4.62 (2H, s), 5.38 (1H, d, J=4.5), 5.48 (2H, ABq), 5.89 (1H, d, J=4.5), 6.84 (1H, s), 8.38 (2H, ABq), 8.94 (1H, s).

EXAMPLE 10

7-[(Z)-2-(2-Aminothiazol-4-yl)-2-methoxyiminoacetamido]-3-[{5-(2-methylthiazolo[4,5-c]pyridinio)}methyl]-3-cephem-4-carboxylate (Ih)

A mixture of benzhydryl 3-iodomethyl-7-[(Z)-2-methoxyimino-2-(2-tritylaminothiazol-4-yl)acetamido]-3-cephem-4-carboxylate [VIIa] (466 mg, 0.5 mmole) and 2-methylthiazolo[4,5-c]pyridine (100 mg, 0.67 mmole) in 2.5 mL of DMSO was stirred at room temperature for an hour and diluted with ether (150 mL). The resulting oil was triturated with ether and the solvent was decanted. This procedure was repeated another three times. A solution of the residual precipitate in 50 mL of CHCl$_3$—CH$_3$OH (4:1) was filtered and evaporated, and the residue was triturated with isopropyl ether (50 mL) to afford 558 mg of the quaternized blocked cephalosporin ($\nu^{KBr}$ cm$^{-1}$: 1785, 1720, 1670, 1625, 1525, 1030), which was treated with anisole (0.5 mL) and 90% TFA (5 mL) with cooling in an ice-water bath. The mixture was stirred at room temperature for 1.5 hours and evaporated below 40° C. The residue was triturated with isopropyl ether (30 mL) to give 395 mg of a yellow powder. The crude powder was dissolved in a mixture of 98% formic acid (2 mL) and concentrated hydrochloric acid (0.1 mL), and the solution was allowed to stand at room temperature for 30 minutes. The resulting mixture was chromatographed on a column of HP-20 resin (100 mL) by eluting with water and 30% CH$_3$OH successively. The fractions containing the desired product were combined, concentrated and lyophilized to give 161 mg (59%) of the title compound (Ih) as a yellow amorphous powder. Estimated purity 65% (by HPLC).

IR: $\nu_{max}^{KBr}$ cm$^{-1}$ 1770, 1660, 1620, 1535.

UV: $\nu_{max}^{phosphate\ buffer\ pH\ 7}$ nm($\epsilon$) 228 (50300), 260 (22000).

NMR: $\delta^{D2O}$ ppm 3.06 (3H, s), 3.51 (2H, ABq), 4.04 (3H, s), 5.36 (1H, d, J=4), 5.61 (2H, ABq), 5.84 (1H, d, J=4), 6.75 (1H, s), 8.72 (2H, ABq), 9.68 (1H, s).

EXAMPLE 11

7-[(Z)-2-(2-Aminothiazol-4-yl)-2-methoxyiminoacetamido]-3-[{5-(2-methylthiothiazolo[4,5-c]pyridinio)}methyl]-3-cephem-4-carboxylate (Ii)

A mixture of benzhydryl 3-iodomethyl-7-[(Z)-2-methoxyimino-2-(2-tritylaminothiazol-4-yl)acetamido]-3-cephem-4-carboxylate [VIIa] (470 mg, 0.51 mmole) and 2-methylthiothiazolo[4,5-c]pyridine (121 mg, 0.66 mmole) in 3 mL of dry DMSO was allowed to stand for 30 minutes at room temperature. The reaction mixture was diluted with ethyl acetate (30 mL), washed with water (3×20 mL) and aqueous NaCl, dried over anhydrous Na$_2$SO$_4$ and concentrated under reduced pressure. The residue was treated with ethyl ether and filtered to give 475 mg of the quaternized blocked cephalosporin, which was dissolved in 3 mL of TFA (99%) and allowed to stand for 1.5 hours at ambient temperature. Removal of the solvent followed by trituration with isopropyl ether (30 mL) gave 360 mg of the TFA salt of Ii as a powder. The TFA salt was chromatographed on a column of HP-20 resin and eluted with water (300 mL), 10% CH$_3$OH—H$_2$O (300 mL) and 30% CH$_3$OH—H$_2$O (300 mL), successively. Fractions eluted with 30% CH$_3$OH—H$_2$O were combined, concentrated in vacuo and lyophilized to afford 136 mg (25%) of the title compound (Ii). Estimated purity 50% (by HPLC).

IR: $\nu_{max}^{KBr}$ cm$^{-1}$ 1770, 1660, 1615, 1530.

UV: $\nu_{max}^{phosphate\ buffer\ pH\ 7}$ nm($\epsilon$) 262 (36900), 294 (16500).

NMR: $\delta^{D2O}$ ppm 2.91 (3H, s, —SCH$_3$), 3.50 (2H, m, 2-CH$_2$), 4.09 (3H, s, =N—OCH$_3$), 5.37 (1H, d, J=5, 6-H), 5.71 (2H, ABq, 3-CH$_2$), 5.87 (1H, d, J=5, 7-H), 6.86 (1H, s, thiazole-5-H), 8.55 (1H, d, J=6, thiazolopyridinio-7'-H), 8.81 (1H, d, J=6, thiazolopyridinio-6'-H), 9.50 (1H, s, thiazolopyridinio-4'-H).

EXAMPLE 12

7-[(Z)-2-(2-Aminothiazol-4-yl)-2-ethoxyiminoacetamido]-3-[{5-(2-aminothiazolo[4,5-c]pyridinio)}methyl]-3-cephem-4-carboxylate (Ij)

To a stirred solution of benzhydryl 7-[(Z)-2-ethoxyimino-2-(2-tritylaminothiazol-4-yl)acetamido]-3-iodomethyl-3-cephem-4-carboxylate [VIIb] (600 mg, 0.64 mmole) in 4 mL of DMSO, was added 2-aminothiazolo[4,5-c]pyridine (128 mg, 0.85 mmole). The mixture was stirred at room temperature for 40 minutes and then diluted with ether (100 mL). The oily precipitate which separated was triturated with ethyl ether and the solvent was decanted. This procedure was repeated another four times. A solution of the residual precipitate in 50 mL of CHCl$_3$—CH$_3$OH (4:1) was filtered and the filtrate was concentrated to give an oily residue, which was triturated with isopropyl ether (50 mL). The solid thus obtained was collected by filtration to give 675 mg of the quaternized blocked cephalosporin as yellow powder. The powder was treated with anisole (2 mL) and 90% TFA (11 mL) with ice coling. The mixture was stirred at room temperature for 1.5 hours and evaporated in vacuo. The residue was triturated with isopropyl ether (50 mL) and collected by filtration to give 490 mg of crude Ij, which was purified by column chromatography using HP-20 resin (100 mL). The column was eluted with water and 30% aqueous methanol successively. The desired fractions which were obtained by elution with 30% CH$_3$OH were combined, concentrated and lyophilized to afford 44 mg (13%) of the title compound (Ij) as a yellow amorphous powder. Estimated purity 30% (by HPLC).

IR: $\nu_{max}^{KBr}$ cm$^{-1}$ 1750, 1655sh, 1600, 1520.

UV: $\nu_{max}^{phosphate\ buffer\ pH\ 7}$ nm($\epsilon$) 246 (26800).

EXAMPLE 13

7-[(Z)-2-(2-Aminothiazol-4-yl)-2-(1-carboxycyclobut-1-oxyimino)-acetamido]-3-(2-amino-5-thiazolo[4,5-c]pyridinio)methyl-3-cephem-4-carboxylate (Ik)

A mixture of benzhydryl 7-[(Z)-2-(1-t-butoxycarbonylcyclobut-1-oxyimino)-2-(2-tritylaminothiazol-4-yl)-acetamido]-3-iodomethyl-3-cephem-4-carboxylate [VIIe'] (643 mg, 0.6 mmole) and 2-aminothiazolo[4,5-c]pyridine (100 mg, 0.67 mmole) in 3 ml of dry DMSO was stirred at room temperature for an hour. The reaction mixture was diluted with ether (50 ml) to separate a precipitate, which was triturated with ether (50 ml). The resulting precipitate was dissolved in 30 ml of methylene chloride. After filtration, the filtrate was evaporated and the residue was triturated with isopropyl ether to give 622 mg of the crude blocked quaternary salt as a brown powder. A mixture of the crude solid (450 mg, 0.37 mmole), anisole (0.5 ml), trifluoroacetic acid (5 ml), and water (0.3 ml) was stirred at room temperature for 1.25 hours and concentrated under reduced pressure. The residue was triturated with isopropyl ether (70 ml), and the precipitate was isolated by filtration to give 330 mg of crude final product as a yellow powder, which was dissolved in a mixture of 85% formic acid (1 ml) and concentrated hydrochloric acid (0.05 ml). The solution was allowed to stand at room temperature for 20 minutes and adsorbed on a column of HP-20 resin (40 ml). It was eluted with water (150 ml), 30% aqueous methanol (150 ml) and 50% aqueous methanol (300 ml). Fractions containig the desired product were combined, concentrated and lyophilized to give 167 mg of powder, which was found to be a mixture of the $\Delta^2$ and $\Delta^3$ isomers by NMR and HPLC. It was further purified by column chromatography using the packing of the PrepPAK-500/C$_{18}$ (Waters) (20 ml) and the eluate with water (400 ml) was collected in 10 ml fractions, which were monitored by HPLC. The desired fractions were combined, concentrated and lyophilized to afford 58 mg (20%) of Ik as a pale yellow amorphous powder. Mp >150° C. (dec.). Estimated purity 80% (by HPLC).

IR: $\nu_{max}^{KBr}$ cm$^{-1}$ 1760, 1655(sh), 1600, 1530.

UV: $\nu_{max}^{Phosphate\ buffer\ pH\ 7}$ nm($\epsilon$) 247 (51000), 275 (sh)(19000).

NMR: $\delta^{D2O}$ ppm 1.7–2.6 (6H, m), 3.50 (2H, ABq), 5.36 (1H, d, J=4.5), 5.47 (2H, ABq), 5.86 (1H, d, J=4.5), 6.84 (1H, s), 8.39 (2H, ABq), 8.92 (1H, s).

EXAMPLE 14

7-[(Z)-2-(2-Aminothiazol-4-yl)-2-(1-carboxycyclobut-1-oxyimino)-acetamido]-3-(2-methyl-5-thiazolo[4,5-c]pyridinio)methyl-3-cephem-4-carboxylate (Im)

A mixture of benzhydryl 7-[(Z)-2-(1-t-butoxycarbonylcyclobut-1-oxyimino)-2-(2-tritylaminothiazol-4-yl)acetamido]-3-iodomethyl-3-cephem-4-carboxylate [VIIe'] (482 mg, 0.45 mmole) and 2-methylthiazolo[4,5-c]pyridine (70 mg, 0.47 mmole) in 2 ml of dry DMSO was stirred at room temperature for an hour and diluted with ether (150 ml) to afford an oily precipitate, which was triturated with ether (100 ml×4). A solution of the precipitate in methylene chloride (30 ml) was evaporated under reduced pressure, and the residue was triturated with isopropyl ether (30 ml) to give 421 mg of the crude blocked quaternary salt as a yellow powder. The crude blocked quaternary salt (400 mg, 0.372 mmole) was mixed with anisole (0.5 ml), trifluoroacetic acid (5 ml) and water (0.3 ml) with ice cooling, was stirred at room temperature for 1.5 hours and then concentrated under reduced pressure. The residue was triturated with isopropyl ether (50 ml) to afford 333 mg of the crude title product as yellow powder, which was dissolved in a mixture of 85% formic acid (1 ml) and concentrated hydrochloric acid (0.05 ml). The solution was allowed to stand at room temperature for 20 minutes and then was adsorbed on a column of HP-20 (40 ml). It was eluted with water (200 ml), 30% aqueous methanol (120 ml) and 50% aqueous methanol (200 ml). The desired fractions were combined, concentrated and lyophilized to give 138 mg of yellow powder, which was dissolved in a small amount of water by adding sodium bicarbonate. The solution was subjected to column chromatography using the packing of the PrepPAK-500/C$_{18}$ (Waters) (20 ml), and the eluate with water (300 ml) was collected in fractions. The desired fractions were combined, concentrated and lyophilized to give 94 mg (34%) of Im as a pale yellow amorphous powder. Mp >155° C. (dec.). Estimated purity 70% (by HPLC).

IR: $\nu_{max}^{KBr}$ cm$^{-1}$ 1760, 1655 (sh), 1600, 1530.

UV: $\nu_{max}^{Phosphate\ buffer\ pH\ 7}$ nm($\epsilon$) 228 (46300), 260 (20300).

NMR: $\delta^{D2O}$ ppm 1.8–2.7 (6H, m), 3.08 (3H, s), 3.55 (2H, ABq), 5.41 (1H, d, J=4.5), 5.64 (2H, ABq), 5.90 (1H, d, J=4.5), 6.78 (1H, s), 8.74 (2H, ABq), 9.73 (1H, s).

EXAMPLE 15

7-[(Z)-2-(2-Aminothiazol-4-yl)-2-methoxyiminoacetamido]-3-[{5-(2-aminothiazolo[4,5-c]pyridinio)}methyl]-3-cephem-4-carboxylate (In)

To a stirred solution of benzhydryl 3-iodomethyl-7-[(Z)-2-methoxyimino-2-(2-tritylaminothiazol-4-yl)acetamido]-3-cephem-4-carboxylate [VIIa] (466 mg, 0.5 mmole) in 3 mL of DMSO, was added 2-aminothiazolo[4,5-c]pyridine (100 mg, 0.66 mmole). The mixture was stirred at room temperature for 1.2 hours and diluted with ether (50 mL). The deposited oil was triturated with ether and the solvent was decanted. This procedure was repeated another three times. A solution of the residual precipitate in 50 mL of CHCl$_3$—CH$_3$OH (4:1) was filtered and concentrated in vacuo. The residue was triturated in isopropyl ether (50 mL). The precipitate (602 mg) was collected by filtration and treated with anisole (0.5 mL) and 90% TFA with cooling in an ice-water bath. After one hour stirring at room temperature, the mixture was evaporated in vacuo and the residue was triturated with isopropyl ether (50 mL). The precipitate was collected by filtration to give 414 mg of crude If as a tan powder, which was purified by column chromatography on HP-20 resin (100 mL), eluting with water and 30% CH$_3$OH successively. The desired fractions which were eluted with 30% CH$_3$OH, were combined, concentrated and lyophilized to obtain 36 mg (13%) of the title compound (In) as a pale yellow amorphous powder. Estimated purity 60% (by HPLC).

IR: $\nu_{max}^{KBr}$ cm$^{-1}$ 1770, 1640, 1610, 1540.

UV: $\nu_{max}^{phosphate\ buffer\ pH\ 7}$ nm($\epsilon$) 246 (43600).

NMR: $\delta^{DMSO-d6(D2O)}$ ppm 3.78 (3H, s), 5.07 (1H, d, J=4), 5.67 (1H, d, J=4), 6.67 (1H, s), 8.57 (2H, ABq), 9.25 (1H, s).

EXAMPLE 16

7-[(Z)-2-(2-Aminothiazol-4-yl)-2-(2-carboxyprop-2-oxyimino)-acetamido]-3-[{5-(2-aminothiazolo[4,5-c]pyridinio)}methyl]-3-cephem-4-carboxylate (Io)

A mixture of diphenylmethyl 7-[(Z)-2-t-butoxycarbonylprop-2-oxyimino)-2-(2-tritylaminothiazol-4-yl)acetamido]-3-iodomethyl-3-cephem-4-carboxylate [VIId'] (455 mg, 0.43 mmole) and 2-aminothiazolo[4,5-c]pyridine (75 mg, 0.5 mmole) in 2.5 mL of DMSO was stirred for 1.5 hours at room temperature and then treated with ether (50 mL) to separate an oily precipitate, which was triturated with ether. The ether layer was removed by decantation. This procedure was repeated another three times. A solution of the residual precipitate in 30 mL of $CHCl_3-CH_3OH$ (4:1) was filtered, the filtrate was evaporated and the residue was triturated with isopropyl ether. The precipitate (349 mg) was collected by filtration and treated with anisole (0.3 mL) and 90% TFA (3 ml) with ice cooling. The mixture was stirred at room temperature for 1.5 hours and evaporated in vacuo, and the residue was triturated with isopropyl ether (50 ml) to give 280 mg of crude Io as a yellow powder, which was purified by HP-20 resin column chromatography (40 ml). The column was eluted with water and subsequently with 30% aqueous $CH_3OH$. The desired fractions, eluted with 30% $CH_3OH$, were combined, concentrated and lyophilized to afford 19 mg (7%) of the title compound (Io) as a pale yellow amorphous powder. Estimated purity 60% (by HPLC).

IR: $\nu_{max}^{KBr}$ cm$^{-1}$ 1770, 1660sh, 1635, 1540.
UV: $\nu_{max}^{Phosphate\ buffer\ pH\ 7}$ nm($\epsilon$) 247 (41700).
NMR: $\delta^{DMSO-d6(D2O)}$ ppm 1.42 (6H, s), 5.10 (1H, d, J=4), 5.75 (1H, d, J=4), 6.66 (1H, s), 8.54 (2H, ABq), 9.23 (1H, s).

EXAMPLE 17

7-[(Z)-2-(2-Aminothiazol-4-yl)-2-methoxyiminoacetamido]-3-(2-acetylamino-5-thiazolo[4,5-c]pyridinio)methyl-3-cephem-4-carboxylate (Ip)

A. 2-Acetylaminothiazolo[4,5-c]pyridine

To a suspension of 2-aminothiazolo[4,5-c]pyridine [prepared according to the procedure in T. Takahashi et al., Pharm. Bull. (Japan) 2, 34 (1954)] (151 mg, 1 mmole) in acetic anhydride (1 ml) was added pyridine (1 ml), and the mixture was heated at 100°-120° C. for an hour. After cooling, the mixture was diluted with $CH_2Cl_2$ (20 ml). The resulting precipitate was collected by filtration and recrystallized from methanol (20 ml) to give 90 mg of the title compound as fine needles (46%). Mp. >212° C. (sub.).

UV: $\nu_{max}^{MeOH}$ nm($\epsilon$) 223 (25600), 271 (15800).
NMR: $\delta_{max}^{DMSO-d6}$ 2.28 (3H, s), 8.20 (2H, ABq), 8.97 (1H, s).

B. 7-[(Z)-2-(2-Aminothiazol-4-yl)-2-methoxyiminoacetamido]-3-(2-acetylamino-5-thiazolo[4,5-c]pyridinio)methyl-3-cephem-4-carboxylate (Ip)

A mixture of diphenylmethyl 7-[(Z)-2-methoxyimino-2-(2-tritylaminothiazol-4-yl)acetamido]-3-iodomethyl-3-cephem-4-carboxylate [VIIa] (400 mg, 0.43 mmole) and 2-acetylaminothiazolo-[4,5-c]pyridine (82 mg, 0.43 mmole) in 0.8 ml of dry DMSO was allowed to stand at room temperature for 40 minutes. The mixture was diluted with a mixture of ethyl ether, ethyl acetate and diisopropyl ether. The precipitate was collected by filtration to afford 299 mg of crude quaternary salt, which was mixed with 2.5 ml of TFA and 2 drops of anisole. The mixture was stirred for an hour a room temperature and evaporated. The residue was triturated with ether to give 185 mg of crude Ip which was purified by chromatography on an HP-20 resin column (40 ml) using 30% aqueous $CH_3OH$ as an eluant. The fractions containing the desired product were combined, concentrated and lyophilized to afford 105 mg (55%) of Ip, mp. 186°~198° C. (dec.). Estimated purity by HPLC: 80%.

IR: $\nu_{max}^{KBr}$ cm$^{-1}$ 1700, 1660, 1620, 1540.
UV: $\nu_{max}^{Phosphate\ buffer\ (ph\ 7)}$ nm($\epsilon$) 249.5 (47700).
NMR: $\delta_{ppm}^{D2O+NaHCO3}$ 2.4 (3H, s), 3.22 (1H, d, J=16.5), 3.74 (1H, d, J=16.5), 4.0 (3H, s), 5.34 (1H, d, J=5.0), 5.86 (1H, d, J=5.0), 6.85 (1H, s), 8.41 (1H, d, J=7.5), 8.64 (1H, d, J=7.5), 9.25 (1H, s).

EXAMPLE 18

7-[(Z)-2-(2-Aminothiazol-4-yl)-2-methoxyiminoacetamido]-3-(2-glycylamino-5-thiazolo[4,5-c]pyridinio)methyl-3-cephem-4-carboxylate (Iq)

A. 2-(N-t-Butoxycarbonylglycylamino)thiazolo[4,5-c]pyridine

A mixture of 2-aminothiazolo[4,5-c]pyridine (530 mg, 3.5 mmole), 2.0 ml of N,O-bistrimethylsilylacetamide (BSA) and 7 ml of dimethylformamide was heated at 60° C. with stirring. The resulting clear solution was added to the chilled mixed anhydride solution which was prepared from N-t-butyloxycarbonyl glycine (700 mg, 4 mmoles), triethylamine (404 mg, 4 mmoles) and isobutyl chloroformate (546 mg, 4 mmoles) in 10 ml of dry DMF at −10° C. The reaction mixture was stirred 2 days at room temperature and then diluted with water and extracted with 450 ml of ethyl acetate. The extracts were combined, evaporated and triturated with chloroform to give 175 mg of the title compound. Additional product (155 mg) was obtained from the mother liquor. Total yield was 330 mg (30%), which was recrystallized from $CH_3OH$. Mp. 204°~208° C. (dec.).

IR: $\nu_{max}^{KBr}$ cm$^{-1}$ 1690, 1600, 1500, 1355, 1260, 1235, 1150.
UV: $\nu_{max}^{MeOH}$ nm($\epsilon$) 224 (25900), 271 (15500).
NMR: $\delta_{ppm}^{DMSO-d6}$ 1.45 (9H, s), 3.97 (2H, d, J=6.0), 7.19 (1H, br-t, J=6.0), 8.07 (1H, d, J=5.5), 8.43 (1H, d, J=5.5), 9.01 (1H, s), 12.5 (1H, br).

B. 7-[(Z)-2-(2-Aminothiazol-4-yl)-2-methoxyiminoacetamido]-3-(2-glycylamino-5-thiazolo[4,5-c]pyridinio)methyl-3-cephem-4-carboxylate (Iq)

A mixture of diphenylmethyl 7-[(Z)-2-methoxyimino-2-(2-tritylaminothiazol-4-yl)acetamido]-3-iodomethyl-3-cephem-4-carboxylate [VIIa] (237 mg, 0.29 mmole) and 2-(N-t-butoxycarbonylglycylamino)thiazolo[4,5-c]pyridine (95 mg, 0.31 mmole) in 2 ml of dry DMSO was allowed to stand at room temperature for 2 hours and then diluted with ether to give the crude quaternary salt, which was treated with 90% TFA and 2 drops of anisole at room temperature for 30 minutes. The mixture was evaporated and triturated with ether to afford 168 mg of pale yellow precipitate, which was purified by a column of HP-20 resin (40 ml) using 30% aqueous $CH_3OH$ as an eluant to give 88 mg of the title product Iq. Mp. 178°–187° C. (dec.). Estimated purity by HPLC: 60%.

IR: $\nu_{max}^{KBr}$ cm$^{-1}$ 1765, 1660sh, 1610, 1535.

UV: $\nu_{max}^{Phosphate\ buffer\ (pH\ 7)}$ nm($\epsilon$) 267 (33700), 306 (16000).

NMR: $\delta_{ppm}^{D2O+DCl}$ 3.58 (2H, ABq, J=18.5), 4.14 (3H, s), 4.39 (2H, s), 5.39 (1H, d, J=5.5), 5.70 (2H, m), 5.94 (1H, d, J=5.5), 7.19 (1H, s), 8.67 (1H, d, J=6), 8.83 (1H, d, J=6), 9.48 (1H, s).

EXAMPLE 19

7-[(Z)-2-(2-Aminothiazol-4-yl)-2-methoxyiminoacetamido]-3-[2-(3-methylureido)-5-thiazolo[4,5-c]pyridinio]methyl-3-cephem-4-carboxylate (Ir)

A. 2-(3-Methylureido)thiazolo[4,5-c]pyridine

A mixture of 2-aminothiazolo[4,5-c]pyridine (151 mg, 1 mmole), pyridine (1.8 ml), CH$_3$NCO (1.2 ml) and 3 ml DMF was stirred at room temperature for 2 days. To the reaction mixture was added CH$_3$OH, and the mixture was evaporated in vacuo. The residue was treated with CH$_3$OH and ether to give 165 mg (79%) of crystalline solid. Mp. 178°~187° C. (dec.).

IR: $\nu_{max}^{KBr}$ cm$^{-1}$ 3360, 1650, 1580, 1520.

UV: $\nu_{max}^{MeOH}$ nm($\epsilon$) 226.5 (32500), 267.5 (17300).

NMR: $\delta_{ppm}^{DMSO-d6}$ 2.83 (3H, d, J=5.0), 6.69 (1H, q, J=5.0), 7.99 (1H, d, J=5.5), 8.36 (1H, d, J=5.5), 8.89 (1H, s).

B. 7-[(Z)-2-(2-Aminothiazol-4-yl)-2-methoxyiminoacetamido]-3-[2-(3-methylureido)-5-thiazolo[4,5-c]pyridinio]methyl-3-cephem-4-carboxylate (Ir)

A mixture of diphenylmethyl 7-[(Z)-2-methoxyimino-2-(2-tritylaminothiazol-4-yl)acetamido]-3-iodomethyl-3-cephem-4-carboxylate [VIIa] (466 mg, 0.5 mmole) and 2-(3-methylureido)-thiazolo[4,5-c]pyridine (104 mg, 0.5 mmole) in 3 ml of dry DMF was stirred at room temperature for 1 hour and diluted with ether acetate to give 430 mg of crude quaternary salt, which was treated with TFA and anisole at room temperature for 30 minutes. The mixture was evaporated and triturated with ether to give 302 mg of crude Ir which was purified on a column of HP-20 resin (40 ml) using 30% CH$_3$OH as an eluant to give 169 mg (56%) of Ir. Mp. 184°~200° C. (dec.). Estimated purity by HPLC: 40%.

IR: $\nu_{max}^{KBr}$ cm$^{-1}$ 1765, 1690, 1665, 1610, 1535.

UV: $\nu_{max}^{Phosphate\ buffer\ (pH\ 7)}$ nm($\epsilon$) 252 (52700).

NMR: $\delta_{ppm}^{D2O}$ 2.90 (3H, s), 3.48 (2H, ABq, J=18), 4.04 (3H, s), 5.35 (1H, d, J=4.0), 5.46 (2H, ABq, J=13.5), 5.90 (1H, d, J=4.0), 6.99 (1H, s), 8.32 (ABq, J=4.0), 8.82 (1H, s).

EXAMPLE 20

7-[(Z)-2-(2-Aminothiazol-4-yl)-2-methoxyiminoacetamido]-3-(2-methoxycarbonylamino-5-thiazolo[4,5-c]pyridinio)methyl-3-cephem-4-carboxylate (Is)

A. 2-Methoxycarbonylaminothiazolo[4,5-c]pyridine

To a mixture of 2-aminothiazolo[4,5-c]pyridine (50 mg, 0.33 mmole) and 0.4 ml of methylchloroformate in 1 ml of dry DMF was added 0.4 ml of pyridine. The mixture was allowed to stand overnight at room temperature and aqueous NaHCO$_3$ and ethyl acetate were then added. The organic layer was separated, washed with saturated aqueous NaCl solution, dried over Na$_2$SO$_4$ and evaporated in vacuo to give 54 mg (78%) of the title compound, which was recrystallized from CHCl$_3$—CH$_3$OH to give pure crystalline solid. Mp 146°~152° C. (dec.).

IR: $\nu_{max}^{KBr}$ cm$^{-1}$ 1710, 1590, 1405, 1280, 1245.

UV: $\nu_{max}^{MeOH}$ nm($\epsilon$) 223.5 (32000), 265 (15000).

NMR: $\delta_{ppm}^{DMSO-d6}$ 3.91 (3H, s), 8.11 (1H, d, J=5.5), 8.47 (1H, d, J=5.5), 9.08 (1H, s), 12.2 (1H, br).

B. 7-[(Z)-2-(2-Aminothiazol-4-yl)-2-methoxyiminoacetamido]-3-(2-methoxycarbonylamino-5-thiazolo[4,5-c]pyridinio)methyl-3-cephem-4-carboxylate (Is)

A solution of diphenylmethyl 7-[(Z)-2-methoxyimino-2-(2-tritylaminothiazol-4-yl)acetamido]-3-iodomethyl-3-cephem-4-carboxylate [VIIa] (419 mg, 0.45 mmole) and 2-methoxycarbonylaminothiazolo[4,5-c]pyridine (94 mg, 0.45 mmole) in 2 ml of dry DMSO was allowed to stand at room temperature for 1 hour and diluted with ether to give 514 mg of crude quaternary salt, which was treated with 5 ml of TFA and 3 drops of anisole at room temperature for 30 minutes. The mixture was evaporated in vacuo and triturated with ether to afford 338 mg of crude Is which was purified on a column of HP-20 resin (40 ml) using 30% aqueous CH$_3$OH as an eluant to give 95 mg (35%) of Is. Mp. 156°~184° C. (dec.). Estimated purity by HPLC: 40%.

IR: $\nu_{max}^{KBr}$ cm$^{-1}$ 1765, 1655(sh), 1610, 1535.

UV: $\nu_{max}^{Phosphate\ buffer\ (pH\ 7)}$ nm($\epsilon$) 247 (37900), 265 (42800), 303 (16900).

NMR: $\delta_{ppm}^{D2O}$ 3.50 (2H, ABq, J=18), 3.86 (3H, s), 4.03 (3H, s), 5.36 (1H, d, J=5.0), 5.22 (2H, m), 5.90 (1H, d, J=5.0), 6.97 (1H, s), 8.24 (1H, d, J=7.0), 8.48 (1H, d, J=7.0), 8.92 (1H, s).

EXAMPLE 21

7-[(Z)-2-(2-Aminothiazol-4-yl)-2-methoxyiminoacetamido]-3-[2-(pyrrolidin-1-ylcarbonylamino)-5-thiazolo[4,5-c]pyridinio]methyl-3-cephem-4-carboxylate (It)

A. 2-Phenoxycarbonylaminothiazolo[4,5-c]pyridine

To a mixture of 2-aminothiazolo[4,5-c]pyridine (302 mg, 2 mmoles) and pyridine (0.2 ml) in 5 ml of DMF was added phenyl chloroformate (400 mg, 2.5 mmoles), and the mixture was stirred at room temperature for 1.5 days. The crystalline precipitate was collected by filtration to afford 386 mg (71%) of the title compound. Mp. >290° C.

IR: $\lambda_{max}^{KBr}$ cm$^{-1}$ 1715, 1590, 1575.

UV: $\lambda_{max}^{MeOH}$ nm($\epsilon$) 223.5 (37200), 265.5 (18000).

NMR: $\delta_{ppm}^{DMSO-d6}$ 7.4 (5H, s), 8.05 (1H, d, J=5), 8.40 (1H, d, J=5), 9.08 (1H, s).

B. 2-(Pyrrolidin-1-ylcarbonylamino)thiazolo[4,5-c]pyridine

A mixture of 2-phenoxycarbonylaminothiazolo[4,5-c]-pyridine (200 mg, 0.73 mmole) and pyrrolidine (0.3 ml) in DMF (2 ml) was heated at 70° C. for 30 minutes and evaporated in vacuo. The residue was triturated with ether to give 180 mg (98%) of the desired product. Mp. 218°~220° C.

IR: $\nu_{max}^{KBr}$ cm$^{-1}$ 1645, 1590, 1570, 1350, 1255.

UV: $\lambda_{max}^{MeOH}$ nm($\epsilon$) 227.5 (32000), 269 (18400).

NMR: $\delta_{ppm}^{DMSO}$ 1.90 (4H, m), 3.47 (4H, m), 7.97 (1H, d, J=5.5), 8.36 (1H, d, J=5.5), 8.92 (1H, s), 12.2 (1H, br).

C.
7-[(Z)-2-(2-Aminothiazol-4-yl)-2-methoxyiminoacetamido]-3-[2-(pyrrolidin-1-ylcarbonylamino)-5-thiazolo[4,5-c]-pyridinio]methyl-3-cephem-4-carboxylate (It)

A solution of diphenylmethyl 7-[(Z)-2-methoxyimino-2-(2-tritylaminothiazol-4-yl)acetamido]-3-iodomethyl-3-cephem-4-carboxylate [VIIa] (466 mg, 0.5 mmole) and 2-(pyrrolidin-1-yl-carbonylamino)-thiazolo[4,5-c]pyridine (124 mg, 0.5 mmoles) in 2 ml DMSO was allowed to stand at room temperature for 1.5 hours and then triturated with ether to give 606 mg of crude quaternary salt as a powder. The powder was added to a mixture of 5 ml of TFA and 3 drops of anisole and stirred 30 minutes at room temperature. The mixture then was evaporated under reduced pressure and triturated with ether to give 375 mg of crude It, which was purified on a column of HP-20 resin (40 ml) using 50% aqueous $CH_3OH$ as an eluant to give 165 mg (51%) of the desired product It. Mp. 184°~198° C. (dec.). Estimated purity by HPLC: 65%.

IR: $\nu_{max}^{KBr}$ cm$^{-1}$ 1770, 1660, 1610, 1540.

UV: $\lambda_{max}^{Phosphate\ buffer\ (pH\ 7)}$ nm($\epsilon$) 254 (44700), 272(sh) (32000), 312 (13000).

NMR: $\delta_{ppm}^{D_2O}$ 2.0 (4H, br), 3.5 (6H, m), 3.98 (3H, s), 5.34 (1H, d, J=4.5), 5.5 (2H, m), 5.85 (1H, d, J=4.5), 6.86 (1H, s), 8.18 (1H, d, J=6.0), 8.94 (1H, d, J=6.0), 9.42 (1H, s).

EXAMPLE 22
7-[(Z)-2-(2-Aminothiazol-4-yl)-2-methoxyiminoacetamido]-3-(2-dimethylamino-5-thiazolo[4,5-c]pyridinio)methyl-3-cephem-4-carboxylate (Iu)

A. 2-Dimethylaminothiazolo[4,5-c]pyridine

To a suspension of 3-amino-4-mercaptopyridine [prepared according to the procedure of T. Takahashi et al., Pharm. Bull. (Japan) 3, 356 (1955)] (280 mg, 2.5 mmoles) in $CHCl_3$ (5 ml) was added (dichloromethylene)dimethylammonium chloride (400 mg, 2.5 mmoles), and the mixture was heated to reflux for 2 hours. After evaporation of the solvent, the residue was washed with ether, dissolved in water (10 ml) and filtered. The filtrate was adjusted to pH 10 with 2N NaOH, and extracted with $CHCl_3$ (3×30 ml). The $CHCl_3$ extract was dried over $MgSO_4$, and evaporated to give 222 mg of crystalline residue. This product was recrystallized from ether-n-hexane to afford 71 mg of product as needles. Mp. 112°~113° C.

UV: $\lambda_{max}^{MeOH}$ nm($\epsilon$) 231 (32000), 274 (17800). (+HCl) 251 (43900), 290 (12000).

NMR: $\delta_{ppm}^{CDCl_3}$ 3.25 (6H, s), 7.86 (2H, ABq), 8.80 (1H, s).

Anal. Calc'd. for $C_8H_9N_3S$: C, 53.61; H, 5.06; N, 23.44; S, 17.89. Found: C, 53.38, 53.41; H, 5.20, 5.10; N, 23.46, 23.51; S, 18.01, 18.30.

B.
7-[(Z)-2-(2-Aminothiazol-4-yl)-2-methoxyiminoacetamido]-3-(2-dimethylamino-5-thiazolo[4,5-c]pyridinio)methyl-3-cephem-4-carboxylate (Iu)

A mixture of diphenylmethyl 7-[(Z)-2-methoxyimino-2-(2-tritylaminothiazol-4-yl)acetamido]-3-iodomethyl-3-cephem-4-carboxylate [VIIa] (466 mg, 0.5 mmole) and 2-dimethylaminothiazolo[4,5-c]pyridine (90 mg, 0.5 mmole) in dry DMSO (1 ml) was stirred at room temperature for 40 minutes, and diluted with a mixture of ether (20 ml) and ethyl acetate (50 ml). The precipitate was collected by filtration to obtain 517 mg of the crude quaternary salt. The salt was mixed with 0.3 ml of anisole and was treated with 95% TFA under ice cooling. The solution was stirred for an hour at room temperature and evaporated. The residue was triturated with iso-propyl ether and the resulting precipitate was collected by filtration to give 367 mg of the crude title compound as a yellow powder. The crude product was purified by chromatography (HP-20 column 90 ml), eluted with water (200 ml), 30% $CH_3OH$ (240 ml), and 50% $CH_3OH$ (450 ml). The desired fractions were combined, concentrated and lyophilized to give 90 mg of yellow powder, which was further purified by column chromatography by using the packing of Prep-PAK/$C_{18}$ cartridge (50 ml). The column was eluted with water (100 ml) and 30% $CH_3OH$ (200 ml). The desired fractions were concentrated and lyophilized to obtain 40 mg of Iu as pale yellow powder (14% yield). Mp. 119°~123° C. (dec.). Estimated purity by HPLC: 65%.

IR: $\nu_{max}^{KBr}$ cm$^{-1}$ 1770, 1660(sh), 1630, 1580, 1540.

UV: $\lambda_{max}^{Phosphate\ buffer\ (pH\ 7)}$ nm($\epsilon$) 257.5 (51000), 290 (18300).

NMR: $\delta_{ppm}^{DMSO-d_6}$ 3.25 (6H, s), 3.78 (3H, s), 5.05 (2H, m), 5.62 (2H, m), 6.65 (1H, s), 7.12 (2H, br-s), 8.64 (2H, Abq), 9.45 (1H, d, J=8), 9.55 (1H, s).

EXAMPLE 23
7-[(Z)-2-(2-Aminothiazol-4-yl)-2-methoxyiminoacetamido]-3-(2-carboxy-5-thiazolo[4,5-c]pyridinio)methyl-3-cephem-4-carboxylate (Iv)

A mixture of diphenylmethyl 7-[(Z)-2-methoxyimino-2-(2-tritylaminothiazol-4-yl)acetamido]-3-iodomethyl-3-cephem-4-carboxylate [VIIa] (466 mg, 0.5 mmole) and 2-carboxythiazolo[4,5-c]pyridine [prepared according to the procedure of Zhur. Obshchei Khim., 26, 613 (1956); C.A., 50, 13906 (1956)] (90 mg, 0.5 mmole) in 2 ml of DMSO was stirred at room temperature for 1.5 hours and diluted with ethyl acetate-ether to give 375 mg of crude quaternary salt, which was treated with 5 ml of TFA and 0.1 ml of anisole at room temperature for 15 minutes. The mixture was evaporated in vacuo and triturated with ether to give 213 mg of crude Iv. The crude product was dissolved into a small volume of phosphate buffer (pH 7.0) and chromatographed on a column of packing (20 ml) in PrepPAK/$C_{18}$ cartridge. The column was eluted with water (200 ml) and 10% aqueous $CH_3OH$ (150 ml) to afford 51 mg (17%) of the title compound (Iv) as an amorphous powder. Mp. 144°~160° C. (dec.). Estimated purity by HPLC: 85%.

IR: $\nu_{max}^{KBr}$ cm$^{-1}$ 1770, 1625, 1535.

UV: $\lambda_{max}^{Phosphate\ buffer\ (pH\ 7)}$ nm($\epsilon$) 235 (44500), 265(sh) (19400).

NMR: $\delta_{ppm}^{D_2O}$ 3.55 (2H, Abq, J=17.5), 4.05 (3H, s), 5.37 (1H, d, J=4.5), 5.67 (2H, ABq, J=14), 5.91 (1H, d, J=4.5), 6.97 (1H, s), 8.85 (2H, ABq, J=7.0), 9.88 (1H, s).

EXAMPLE 24

7-[(Z)-2-(2-Aminothiazol-4-yl)-2-methoxyiminoacetamido]-3-(2-formylthiazolo[4,5-c]pyridinio)methyl-3-cephem-4-carboxylate (Iw)

A. 2-Formylthiazolo[4,5-c]pyridine

A mixture of 2-methylthiazolo[4,5-c]pyridine [prepared according to the procedure of T. Takahashi et al., Pharm. Bull. (Japan) 2, 196 (1954)] (635 mg, 4.2 mmoles), 2.55 g of $SeO_2$, 10 ml of $CH_3COOH$ and 10 ml of acetic anhydride was heated at 90 100° C. for 2.5 hours, and the reaction mixture then was filtered to remove insolubles. The filtrate was evaporated in vacuo, and purified by a column of $SiO_2$ (50 ml) to give 248 mg (35.5%) of the title compound. Mp. 96.5°~98° C.

IR: $\nu_{max}^{KBr}$ cm$^{-1}$ 1685, 1420, 1250, 875, 855, 795.

UV: $\lambda_{max}^{MeOH}$ nm($\epsilon$) 217 (25000), 242.5 (6400), 271 (2500), 282 (1800).

NMR: $\delta_{ppm}^{CDCl_3}$ 7.95 (1H, d, J=5.5), 8.60 (1H, d, J=5.5), 9.05 (1H, s), 9.42 (1H, s).

B. 7-[(Z)-2-(2-Aminothiazol-4-yl)-2-methoxyiminoacetamido]-3-(2-formylthiazolo[4,5-c]pyridinio)methyl-3-cephem-4-carboxylate (Iw)

A mixture of 2-formylthiazolo[4,5-c]pyridine (85 mg, 0.5 mmole) and diphenylmethyl 7-[(Z)-2-methoxyimino-2-(2-tritylaminothiazol-4-yl)acetamido]-3-iodomethyl-3-cephem-4-carboxylate [VIIa] (466 mg, 0.5 mmole) in 5 ml of ethyl acetate containing 2 drops of DMSO was allowed to stand overnight at room temperature and then diluted with ether to give 418 mg of crude quaternary salt. The salt was treated with 3 ml of TFA and 3 drops of anisole at room temperature for 30 minutes. The mixture was concentrated in vacuo and triturated with ether to give 283 mg of powder, which was purified by a column of packing (20 ml) in Prep-PAK/$C_{18}$ cartridge (for Water's System 500) using 200 ml of water and 5% aqueous $CH_3OH$ (200 ml) as eluants to give 55 mg (20%) of the title compound Iw. Mp. 135°~139° C. (dec.). Estimated purity by HPLC: 55%.

IR: $\nu_{max}^{KBr}$ cm$^{-1}$ 1770, 1660, 1615, 1540.

UV: $\lambda_{max}^{Phosphate\ buffer\ (pH\ 7)}$ nm($\epsilon$) 225 (37500), 260(sh) (19700).

NMR: $\delta_{ppm}^{D_2O}$ 3.51 (2H, ABq), 5.36 (1H, d, J=5.5), 5.67 (2H, ABq), 5.89 (1H, d, J=5.5), 6.96 (1H, s), 8.88 (2H, ABq), 9.87 (1H, s), 9.89 (1H, s).

EXAMPLE 25

7-[(Z)-2-(2-Aminothiazol-4-yl)-2-methoxyiminoacetamido]-3-(2-carbamoyl-5-thiazolo[4,5-c]pyridinio)methyl-3-cephem-4-carboxylate (Ix)

A mixture of diphenylmethyl 7-[(Z)-2-methoxyimino-3-(2-tritylaminothiazol-4-yl)acetamido]-3-iodomethyl-3-cephem-4-carboxylate [VIIa] (466 mg, 0.5 mmole) and 2-carbamoylthiazolo[4,5-c]pyridine [prepared according to the procedure of Zhur. Obshchei Khim., 613 (1956); C.A., 50, 13906 (1956)] (90 mg, 0.5 mmole) in 1 ml of DMSO was stirred at room temperature for 2 hours and diluted with ether to give 593 mg of quaternary salt, which was treated with 5 ml of TFA and 3 drops of anisole at room temperature for 30 minutes. The mixture was evaporated and triturated with ether to give 353 mg of yellow powder, which was purified by a column of packing (20 ml) in PrepPAK/$C_{18}$ cartridge (Water's System 500) using 200 ml of water, 5% aqueous $CH_3OH$ (400 ml) and 10% aqueous $CH_3OH$ (300 ml) as eluant to give 115 mg (40%) of the title product (Ix). Mp. 169°~173° C. (dec.). Estimated purity by HPLC: 65%.

IR: $\nu_{max}^{KBr}$ cm$^{-1}$ 1765, 1670, 1610, 1535.

UV: $\lambda_{max}^{Phosphate\ buffer\ (pH\ 7)}$ nm($\epsilon$) 236 (50900).

NMR: $\delta_{ppm}^{DMSO-d_6+D_2O}$ 3.75 (3H, s), 5.03 (1H, d, J=5.0), 5.64 (1H, d, J=5.0), 6.66 (1H, s), 8.84 (1H, d, J=7.0), 9.24 (1H, d, J=7.0), 10.44 (1H, s).

EXAMPLE 26

7-[(Z)-2-(2-Aminothiazol-4-yl)-2-methoxyiminoacetamido]-3-[(2-methylamino-5-thiazolo[4,5-c]pyridinio)methyl]-3-cephem-4-carboxylate (Iy)

A solution of $AgClO_4$ (207 mg, 1.0 mmole) in THF (1 ml) was added in approximately four equal portions, during one hour, to a stirred solution at 25° C. of benzhydryl 3-iodomethyl-7-[(Z)-2-methoxyimino-2-(2-tritylaminothiazol-4-yl)acetamido]-3-cephem-4-carboxylate [VIIa] (913 mg, 1.0 mmole) and 2-methylaminothiazolo[4,5-c]pyridine (165 mg, 1.0 mmole) in THF (8 ml). Stirring was continued for an additional hour. The mixture was filtered through diatomaceous earth and the filtrate concentrated. A solution of the residue in $CH_2Cl_2$ was washed with dilute aqueous HCl and then with brine. The $CH_2Cl_2$ layer was dried over $Na_2SO_4$ and concentrated to leave the crude protected quaternized cephalosporin as a brown froth. Concentrated HCl (0.5 ml) was added to a stirred solution of the froth in 95–97% formic acid (15 ml) at 25° C. The solution was stirred for 50 minutes and then was diluted with $H_2O$ (20 ml). The resulting mixture was filtered and the filtrate concentrated on a rotary evaporator. The residue was suspended in $H_2O$ (20 ml), and the pH of the stirred mixture was adjusted to 5.1 with dilute NaOH. The mixture was filtered and the product isolated from the filtrate by high performance low pressure liquid chromatography (HPLPLC). The filtrate was applied to a glass column (300×22 mm) which was packed with Waters PrepPAK-500/$C_{18}$. The column was eluted first with $H_2O$ and then with $H_2O$-10% acetonitrile to elute the title compound. The appropriate fractions were combined and partially concentrated to remove the $CH_3CN$. The aqueous solution was lyophilized to afford 154 mg of the title compound (Iy).

IR: $\nu_{max}^{KBr}$ cm$^{-1}$ 3300, 1775, 1660, 1630, 1525, 1405, 1320, 1030.

NMR: $\delta_{ppm}^{D_2O}$ 3.15 (3H, s, N-$CH_3$), 3.32 (1H, d, 18 Hz, 2-H), 3.72 (1H, d, 18 Hz, 2-H), 4.08 (3H, s, O-$CH_3$), 5.3–5.9 (2H, m, N$^+CH_2$), 5.35 (1H, d, 4.5 Hz, 6-H), 5.87 (1H, d, 4.5 Hz, 7-H), 7.12 (1H, s, thiazole-H), 8.26 (1H, d, 6 Hz, thiazolopyridine 7-H), 8.46 (1H, m, 1 Hz, 6 Hz, thiazolopyridine 6-H), 8.80 (1H, d, 1 Hz, thiazolopyridine-4H).

EXAMPLE 27

7-[(Z)-2-(2-Aminothiazol-4-yl)-2-methoxyiminoacetamido]-3-[(2-N-formylamino-5-thiazolo[4,5-c]pyridinio)methyl]-3-cephem-4-carboxylate (Iz1)

and

7-[(Z)-2-(2-Aminothiazol-4-yl)-2-methoxyiminoacetamido]-3-[(2-dimethylaminomethylimino-5-thiazolo[4,5-c]pyridinio)methyl]-3-cephem-4-carboxylate (Iz2)

A.
2-Dimethylaminomethyliminothiazolo[4,5-c]pyridine

A stirred mixture of 2-aminothiazolo[4,5-c]pyridine [prepared according to the procedure of H. W. Altland and G. A. Molander, J. Heterocyclic Chem., 14, 129 (1977)] (0.5 g, 3.3 mmole) and N,N-dimethylformamide dimethyl acetal (5 ml) was stirred at an oil bath temperature of 80° C. for two hours under an atmosphere of argon. The solution was concentrated to dryness to leave the crystalline product. The solid was triturated with cold petroleum ether and dried to afford 0.55 g (80.9%) of the title compound, mp. 125°–127° C.

B.
7-[(Z)-2-(2-Aminothiazol-4-yl)-2-methoxyiminoacetamido]-3-[(2-N-formylamino-5-thiazolo[4,5-c]pyridinio)methyl]-3-cephem-4-carboxylate (Iz1)

and

7-[(Z)-2-(2-Aminothiazol-4-yl)-2-methoxyiminoacetamido]-3-[(2-dimethylaminomethylimino-5-thiazolo[4,5-c]pyridinio)-methyl]-3-cephem-4-carboxylate (Iz2)

A solution of benzhydryl 3-iodomethyl-7-[(Z)-2-methoxy-imino-2-(2-tritylaminothiazol-4-yl)acetamido]-3-cephem-4-carboxylate [VIIa] (913 mg, 1.0 mmole) and 2-dimethylaminomethyliminothiazolo[4,5-c]pyridine (226.9 mg, 1.1 mmoles) in THF (4 ml) was stirred for two hours at 25° C. The solution was partially concentrated and then was poured into stirred ethyl ether to precipitate the crude protected quaternized cephalosporin (1.08 g) as a brown powder. The protected product was added to a stirred mixture, at 25° C., of 95–97% formic acid (15 ml) and concentrated HCl (0.8 ml). Stirring was continued for one hour. The mixture was diluted with H$_2$O and filtered. The filtrate was concentrated to about 5 ml and was then poured into stirred acetone to precipitate the deprotected products. The yellow solid was dissolved in H$_2$O and the two major products separated by high performance low pressure liquid chromatography utilizing a glass column (300×22 mm) packed with Waters PrepPAK-500/C$_{18}$. The column was eluted sequentially with H$_2$O, H$_2$O-6% CH$_3$CN, H$_2$O-10% CH$_3$CN and H$_2$O-15% CH$_3$CN to afford the product with the shorter retention time, 7-[(Z)-2-(2-aminothiazol-4-yl)-2-methoxyiminoacetamido]-3-[(2-N-formylamino-5-thiazolo[4,5-c]pyridinio)methyl]-3-cephem-4-carboxylate (52 mg) (Iz1)

IR: $\nu_{max}^{KBr}$ cm$^{-1}$ 3400, 1780, 1670, 1630, 1535, 1280, 1030.

NMR: $\delta_{ppm}^{DMSO}$ 3.0–4.0 (2H, m, 2-H), 3.80 (3H, s, OCH$_3$), 5.0–5.9 (4H, m, N$\oplus$CH$_2$, 6-H, 7-H), 6.70 (1H, s, thiazole-H), 7.17 (2H, s, NH$_2$), 8.91 (1H, d, 6 Hz, thiazolopyridine 7-H), 9.06 (1H, s, thiazolopyridine 4-H), 9.32 (1H, d, 6 Hz, thiazolopyridine 6-H), 9.74 (1H, d, 7 Hz, amide N-H), 10.26 (1H, s, aldehyde C-H) and the product with the longer retention time, 7-[(Z)-2-(2-aminothiazol-4-yl)-2-methoxyiminoacetamido]-3-[(2-dimethylaminomethylimino-5-thiazolo[4,5-c]pyridinio)-methyl]-3-cephem-4-carboxylate (89 mg) (Iz2).

IR: $\nu_{max}^{KBr}$ cm$^{-1}$ 3300, 2920, 1775, 1625, 1510, 1465, 1400.

NMR: $\delta_{ppm}^{DMSO,D2O}$ 3.10 (3H, s,

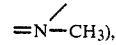

=N—CH$_3$), 3.23 (3H, s,

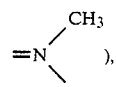

), 3.82 (3H, s, OCH$_3$), 5.06 (1H, d, 4.5 Hz, 6-H), 5.6 (1H, d, 4.5 Hz, 7-H), 6.71 (1H, s, thiazole-H), 8.42 (1H, d, 6 Hz, thiazolopyridine 7-H), 8.63 (1H, s, thiazolopyridine 4-H), 8.80 (1H, d, 6 Hz, thiazolopyridine 6-H).

We claim:

1. A compound of the formula

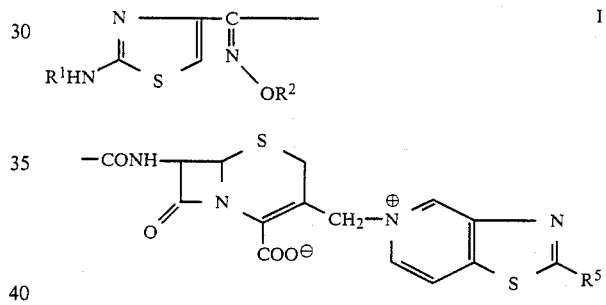

wherein R$^1$ is hydrogen or a conventional amino-protecting group, R$^2$ is a straight or branched chain alkyl group containing from 1 to 4 carbon atoms, allyl, propargyl, 2-butenyl, 2-butynyl, 3-butenyl, 3-butynyl, cyclo(lower)alkyl or a group of the formula

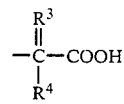

in which R$^3$ and R$^4$ each are independently hydrogen, methyl or ethyl, or R$^3$ and R$^4$, taken together with the carbon atom to which they are attached, may be a cycloalkylidene ring containing from 3 to 5 carbon atoms, and R$^5$ is hydrogen, carboxy, formyl, amino, carbamoyl, (lower)alkylamino, di(lower)alkylamino, guanidino, amidino, (lower)alkyl, (lower)alkoxy, (lower)alkylthio or a group of the formula

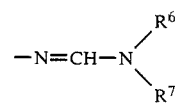

in which R$^6$ and R$^7$ each are independently hydrogen or (lower)alkyl, or when taken together with the nitrogen atom to which they are attached, $R^6$ and $R^7$ represent a 5 to 7-membered saturated ring optionally containing an additional hetero atom selected from N, O and S, or $R^5$ is a group of the formula

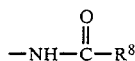

in which $R^8$ is hydrogen, (lower)alkyl, amino(lower)alkyl, (lower)alkoxy, amino, (lower)alkylamino or

in which $R^9$ and $R^{10}$ are each (lower)alkyl or, when taken together with the nitrogen atom to which they are attached, $R^9$ and $R^{10}$ represent a 5 to 7-membered saturated ring optionally containing an additional hetero atom selected from N, O and S; or a nontoxic pharmaceutically acceptable salt, physiologically hydrolyzable ester or solvate thereof.

2. A compound of claim 1 wherein $R^1$ is hydrogen and $R^2$ is methyl, ethyl, allyl, propargyl, carboxymethyl or a group of the formula

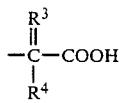

in which $R^3$ and $R^4$ each are methyl, or $R^3$ and $R^4$, taken together with the carbon atom to which they are attached, are cyclopropylidene or cyclobutylidene, or a nontoxic pharmaceutically acceptable salt, physiologically hydrolyzable ester or solvate thereof.

3. A compound of claim 1 wherein $R^1$ is hydrogen, $R^2$ is methyl, ethyl, 2-carboxyprop-2-yl, propargyl, carboxymethyl or 1-carboxycyclobut-1-yl, and $R^5$ is hydrogen, methyl, formyl, carbo(lower)alkoxyamino, (lower)alkanoylamino, glycylamino, di(lower)alkylamino, formylamino, carbamoyl or amino, or a nontoxic pharmaceutically acceptable salt, physiologically hydrolyzable ester or solvate thereof.

4. The compound of claim 1 which is 7-[(Z)-2-(2-aminothiazol-4-yl)-2-methoxyiminoacetamido]-3-{(5-thiazolo[4,5-c]-pyridinio)methyl}-3-cephem-4-carboxylate, or a nontoxic pharmaceutically acceptable salt, physiologically hydrolyzable ester or solvate thereof.

5. The compound of claim 1 which is 7-[(Z)-2-(2-aminothiazol-4-yl)-2-(2-carboxyprop-2-oxyimino)acetamido]-3-{(5-thiazolo[4,5-c]pyridinio)-methyl}-3-cephem-4-carboxylate, or a nontoxic pharmaceutically acceptable salt, physiologically hydrolyzable ester or solvate thereof.

6. The compound of claim 1 which is 7-[(Z)-2-(2-aminothiazol-4-yl)-2-ethoxyiminoacetamido]-3-{(5-thiazolo[4,5-c]pyridinio)methyl}-3-cephem-4-carboxylate, or a nontoxic pharmaceutically acceptable salt, physiologically hydrolyzable ester or solvate thereof.

7. The compound of claim 1 which is 7-[(Z)-2-(2-aminothiazol-4-yl)-2-(1-carboxycyclobut-1-oxyimino)acetamido]-3-{(5-thiazolo[4,5-c]pyridinio)-methyl}-3-cephem-4-carboxylate, or a nontoxic pharmaceutically acceptable salt, physiologically hydrolyzable ester or solvate thereof.

8. The compound of claim 1 which is 7-[(Z)-2-(2-aminothiazol-4-yl)-2-methoxyiminoacetamido]-3-[{5-(2-aminothiazolo[4,5-c]pyridinio)}methyl]-3-cephem-4-carboxylate, or a nontoxic pharmaceutically acceptable salt, physiologically hydrolyzable ester or solvate thereof.

9. The compound of claim 1 which is 7-[(Z)-2-(2-aminothiazol-4-yl)-2-methoxyiminoacetamido]-3-[{5-(2-methylthiazolo[4,5-c]pyridinio)}methyl]-3-cephem-4-carboxylate, or a nontoxic pharmaceutically acceptable salt, physiologically hydrolyzable ester or solvate thereof.

10. The compound of claim 1 which is 7-[(Z)-2-(2-aminothiazol-4-yl)-2-(propargyloxyimino)acetamido]-3-(2-amino-5-thiazolo[4,5-c]pyridinio)methyl-3-cephem-4-carboxylate, or a nontoxic pharmaceutically acceptable salt, physiologically hydrolyzable ester or solvate thereof.

11. The compound of claim 1 which is 7-[(Z)-2-(2-aminothiazol-4-yl)-2-(carboxymethoxyimino)acetamido]-3-(2-amino-5-thiazolo[4,5-c]pyridinio)methyl-3-cephem-4-carboxylate, or a nontoxic pharmaceutically acceptable salt, physiologically hydrolyzable ester or solvate thereof.

12. The compound of claim 1 which is 7-[(Z)-2-(2-aminothiazol-4-yl)-2-(1-carboxycyclobut-1-oxyimino)acetamido]-3-(2-amino-5-thiazolo[4,5-c]pyridinio)methyl-3-cephem-4-carboxylate, or a nontoxic pharmaceutically acceptable salt, physiologically hydrolyzable ester or solvate thereof.

13. The compound of claim 1 which is 7-[(Z)-2-(2-aminothiazol-4-yl)-2-(1-carboxycyclobut-1-oxyimino)acetamido]-3-(2-methyl-5-thiazolo[4,5-c]pyridinio)methyl-3-cephem-4-carboxylate, or a nontoxic pharmaceutically acceptable salt, physiologically hydrolyzable ester or solvate thereof.

14. The compound of claim 1 which is 7-[(Z)-2-(2-aminothiazol-4-yl)-2-allyloxyiminoacetamido]-3-[{5-(thiazolo[4,5-c]pyridinio)}methyl]-3-cephem-4-carboxylate, or a nontoxic pharmaceutically acceptable salt, physiologically hydrolyzable ester or solvate thereof.

15. The compound of claim 1 which is 7-[(Z)-2-(2-aminothiazol-4-yl)-2-(2-carboxyprop-2-oxyimino)acetamido]-3-[{5-(2-aminothiazolo[4,5-c]pyridinio)}methyl]-3-cephem-4-carboxylate, or a nontoxic pharmaceutically acceptable salt, physiologically hydrolyzable ester or solvate thereof.

16. The compound of claim 1 which is 7-[(Z)-2-(2-aminothiazol-4-yl)-2-methoxyiminoacetamido]-3-(2-acetylamino-5-thiazolo[4,5-c]pyridinio)methyl-3-cephem-4-carboxylate, or a nontoxic pharmaceutically acceptable salt, physiologically hydrolyzable ester or solvate thereof.

17. The compound of claim 1 which is 7-[(Z)-2-(2-aminothiazol-4-yl)-2-methoxyiminoacetamido]-3-(2-glycylamino-5-thiazolo[4,5-c]pyridinio)methyl-3-cephem-4-carboxylate, or a nontoxic pharmaceutically acceptable salt, physiologically hydrolyzable ester or solvate thereof.

18. The compound of claim 1 which is 7-[(Z)-2-(2-aminothiazol-4-yl)-2-methoxyiminoacetamido]-3-(2-dimethylamino-5-thiazolo[4,5-c]pyridinio)methyl-3-cephem-4-carboxylate, or a nontoxic pharmaceutically acceptable salt, physiologically hydrolyzable ester or solvate thereof.

19. The compound of claim 1 which is 7-[(Z)-2-(2-aminothiazol-4-yl)-2-methoxyiminoacetamido]-3-(2-formyl-5-thiazolo[4,5-c]pyridinio)methyl-3-cephem-4-carboxylate, or a nontoxic pharmaceutically acceptable salt, physiologically hydrolyzable ester or solvate thereof.

20. The compound of claim 1 which is 7-[(Z)-2-(2-aminothiazol-4-yl)-2-methoxyiminoacetamido]-3-(2-carbamoyl-5-thiazolo[4,5-c]pyridinio)methyl-3-cephem-4-carboxylate, or a nontoxic pharmaceutically acceptable salt, physiologically hydrolyzable ester or solvate thereof.

21. A method of combatting bacterial infection in a warm-blooded animal in need of such treatment comprising administering to said warm-blooded mammal an antibacterially effective amount of at least one compound of claim 1.

22. An antibacterial composition comprising an antibacterially effective amount of at least one compound of claim 1 and an inert pharmaceutical carrier.

23. An antibacterial composition in unit dosage form comprising from about 50 mg to about 1500 mg of at least one compound of claim 1 and an inert pharmaceutical carrier.

* * * * *

UNITED STATES PATENT AND TRADEMARK OFFICE
CERTIFICATE OF CORRECTION

PATENT NO. : 4,500,526
DATED : February 19, 1985
INVENTOR(S) : Kiyoto Imae et al.

It is certified that error appears in the above—identified patent and that said Letters Patent is hereby corrected as shown below:

The substituent group shown at Column 1, Line 37, Column 3, Line 57, Column 5, Line 27, Column 14, Line 48, Column 16, Line 47, Column 18, Line 49, Column 46, Line 50 and Column 47, Line 31, should read as follows:

$$\begin{array}{c} R^3 \\ | \\ -C-COOH \\ | \\ R^4 \end{array}$$

Signed and Sealed this

Second Day of July 1985

[SEAL]

Attest:

DONALD J. QUIGG

Attesting Officer — Acting Commissioner of Patents and Trademarks